(12) United States Patent
Kobayashi et al.

(10) Patent No.: US 9,636,346 B2
(45) Date of Patent: *May 2, 2017

(54) ALPHA-OXOACYL AMINO-CAPROLACTAM DERIVATIVE

(71) Applicant: Seikagaku Corporation, Tokyo (JP)

(72) Inventors: Nobuo Kobayashi, Tokyo (JP); Tsuneo Koji, Tokyo (JP); Hisatomo Kunii, Tokyo (JP); Mizuho Ishikawa, Tokyo (JP); Daisuke Morita, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/263,969

(22) Filed: Sep. 13, 2016

(65) Prior Publication Data
US 2016/0375031 A1  Dec. 29, 2016

Related U.S. Application Data

(63) Continuation of application No. 14/898,242, filed as application No. PCT/JP2014/003158 on Jun. 13, 2014, now Pat. No. 9,481,707.

(30) Foreign Application Priority Data

Jun. 14, 2013  (JP) .................................. 2013-125181

(51) Int. Cl.
A61K 38/00 (2006.01)
A61K 31/55 (2006.01)
C07K 5/02 (2006.01)
C07K 5/065 (2006.01)

(52) U.S. Cl.
CPC ............ A61K 31/55 (2013.01); C07K 5/0202 (2013.01); C07K 5/06078 (2013.01); *A61K 38/00* (2013.01)

(58) Field of Classification Search
CPC ..................................................... A61K 38/00
See application file for complete search history.

(56) References Cited

U.S. PATENT DOCUMENTS

| | | |
|---|---|---|
| 3,740,405 A | 6/1973 | Kraft |
| 6,117,870 A | 9/2000 | Hosoda et al. |

FOREIGN PATENT DOCUMENTS

| | | |
|---|---|---|
| JP | 49-831 B1 | 1/1974 |
| JP | 1974000831 A | 1/1974 |
| JP | 2000204071 A | 7/2000 |
| JP | 2007-236327 A | 9/2007 |
| WO | 9801133 A1 | 1/1998 |
| WO | 0158886 A1 | 8/2001 |
| WO | 03075836 A2 | 9/2003 |

OTHER PUBLICATIONS

International Search Report for corresponding International Application Ser. No. PCT/JP2014/003158, filed Jun. 13, 2014, 2 pages.
Inaoka T et al. Molecular cloning of human cDNA for cathepsin K: novel cysteine proteinase predominantly expressed in bone. Biochem Biophys Res Commun. Jan. 5, 1995;206(1):89-96.
Drake FH et al. Cathepsin K, but not cathepsins B, L, or S, is abundantly expressed in human osteoclasts. J Biol Chem. May 24, 1996;271(21):12511-6.
Gelb BD et al. Pycnodysostosis, a lysosomal disease caused by cathepsin K deficiency. Science. Aug. 30, 1996;273(5279):1236-8.
Brömme D et al, Human cathepsin O2, a matrix protein-degrading cysteine protease expressed in osteoclasts. Functional expression of human cathepsin O2 in Spodoptera frugiperda and characterization of the enzyme. J Biol Chem. Jan. 26, 1996;271(4):2126-32.
Aibe K et al., Substrate specificity of recombinant osteoclast-specific cathepsin K from rabbits. Biol Pharm Bull. Aug. 1996;19(8):1026-31.
McGrath ME et al., Crystal structure of human cathepsin K complexed with a potent inhibitor. Nat Struct Biol. Feb. 1997;4(2):105-9.
Palmer JT et al., Vinyl sulfones as mechanism-based cysteine protease inhibitors. J Med Chem. Aug. 18, 1995;38(17):3193-6.
Brömme D et al., Peptide methyl ketones as reversible inhibitors of cysteine proteinases. J Enzyme Inhib.
Tsujinaka T et al., Synthesis of a new cell penetrating calpain inhibitor (calpeptin). Biochem Biophys Res Commun. Jun. 30, 1988;153(3):1201-8.
Hashida S et al., Inhibitions by E-64 derivatives of rat liver cathepsin B and cathepsin L in vitro and in vivo. J Biochem. Dec. 1980;88(6):1805-11.
Zhao B. et al., Crystal structure of human osteoclast cathepsin K complex with E-64. Nat Struct Biol. Feb. 1997;4(2):109-11.
Thompson SK et al., Design of potent and selective human cathepsin K inhibitors that span the active site. Proc Natl Acad Sci U S A. Dec. 23, 1997;94(26):14249-54.

(Continued)

*Primary Examiner* — Bruck Kifle
(74) *Attorney, Agent, or Firm* — Mintz Levin Cohn Ferris Glovsky and Popeo, P.C.; Peter F. Corless; Christopher R. Cowles

(57) ABSTRACT

The purpose of the present invention is to provide a pharmaceutical composition that is useful for the treatment of diseases that are caused by an increase in bone resorption and that does not cause serious side effects even when used in combination with another drug. The present invention relates to: an α-oxoacyl amino-caprolactam derivative that is represented by formula (I)

(I)

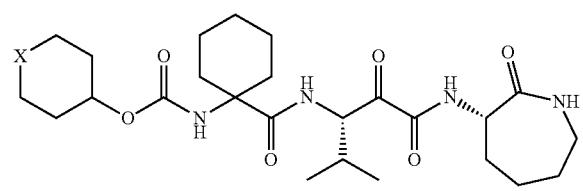

(in the formula, X is —O— or —N(R$^1$)— and R$^1$ represents an alkoxycarbonyl group having 1-10 carbon atoms); and a bone resorption inhibitor containing the α-oxoacyl amino-caprolactam derivative.

4 Claims, No Drawings

(56) References Cited

OTHER PUBLICATIONS

DesJarlais R. et al., Use of X-ray Co-crystal Structures and Molecular Modeling To Design Potent and Selective Non-peptide Inhibitors of Cathepsin K.., J. Am. Chem. Soc., 1998, 120 (35), pp. 9114-9115.
Marquis RW. et al., Conformationally constrained 1,3-diamino ketones: a series of potent inhibitors of the cysteine protease cathepsin K. J Med Chem. Sep. 10, 1998;41(19):3563-7.
Barrett DG. et al., Potent and selective P2-P3 ketoamide inhibitors of cathepsin K with good pharmacokinetic properties via favorable P1', P1, and/or P3 substitutions. Bioorg Med Chem Lett. Oct. 4, 2004;14(19):4897-902.
White RE. High-throughput screening in drug metabolism and pharmacokinetic support of drug discovery. Annu Rev Pharmacol Toxicol. 2000;40:133-57. Review.
Clinical Pharmacokinetics, 71-85, 173-228.
Yoshinori K. [Drug-drug interactions resulting from inhibition of cytochrome P450s]. Nihon Yakurigaku Zasshi. Nov. 2009;134(5):285-8. Japanese.
Salminen KA. et al., Inhibition of human drug metabolizing cytochrome P450 enzymes by plant isoquinoline alkaloids. Phytomedicine. Apr. 15, 2011;18(6):533-8. doi: 10.1016/j.phymed.2010.08.012. Epub Sep. 20, 2010.
International Preliminary Report on Patentability issued in corresponding International application No. PCT/JP2014/003158, Dec. 15, 2015, 11 pages.

ALPHA-OXOACYL AMINO-CAPROLACTAM DERIVATIVE

RELATED APPLICATIONS

This application is a continuation of U.S. application Ser. No. 14/898,242, filed Dec. 14, 2015, allowed, which is the U.S. national stage pursuant to 35 U.S.C. §371, of Japanese international application Ser. No. PCT/JP2014/003158, filed Jun. 13, 2014 and published in Japanese on Dec. 18, 2014 as publication WO2014/199644 A1, which claims the benefit of priority of Japanese Application No. 2013-125181, filed Jun. 14, 2013, which are hereby expressly incorporated by reference in their entirety.

TECHNICAL FIELD

The present invention relates to a novel α-oxoacylaminocaprolactam derivative. Specifically, the present invention relates to an α-oxoacylaminocaprolactam derivative having the effect of selectively inhibiting cathepsin K, which is the principal cysteine protease particularly involved in bone resorption.

BACKGROUND ART

In recent years, as the aging society rapidly develops, the number of patients with senile diseases, particularly, the number of patients with bone diseases has been steadily increasing. Among them, osteoporosis is a serious problem, which often occurs in women, particularly, postmenopausal women. The accelerated bone resorption caused by the hormone imbalance or the aging process in postmenopausal women is closely involved in the development and progression of bone diseases. Therefore, bone resorption inhibitors are generally used in drug therapy for osteoporosis. However, bone resorption-inhibiting drugs being used currently, such as calcitonin preparations, estrogen preparations, vitamin K preparations, and bisphosphonate preparations, have problems with their therapeutic efficacy, immediate effectivity, side effects, dose compliance, or the like, and there has been a demand for the development of bone resorption inhibitors having the potential to become more effective drugs for treating or preventing osteoporosis.

In the living body, equilibrium is maintained between the concentrations of calcium in the bone and in the blood, and calcium constantly moves between the bone and the blood. Such movement of calcium between the bone and the blood is managed by the dynamic turnover between bone formation and bone resorption. It is known that in the bone resorption process, activated osteoclasts dissolve bone minerals such as calcium while the cysteine proteases released from the osteoclasts decompose the organic components of the bone, such as collagen, so that bone resorption is accelerated. Cysteine proteases such as cathepsins B, H, L, and S are present in the lysosomes of osteoclasts. In 1995, human cathepsin K localized in osteoclasts was isolated and found to be produced more in osteoclasts than other cathepsins (see Non Patent Literatures 1 and 2). It was also found that dwarfism patients with abnormal bone resorption have a mutation of the cathepsin K gene (see Non Patent Literature 3).

Thus, cathepsin K has attracted attention as the principal cysteine protease involved in bone resorption, and cathepsin K inhibitors are increasingly expected as bone resorption inhibitors. Aldehyde derivatives, epoxysuccinic acid derivatives (see Non Patent Literatures 4 and 5), or vinylsulfonic acid derivatives (see Non Patent Literatures 6 and 7) have been previously reported as cathepsin K-inhibiting compounds. Unfortunately, these derivatives are known to have low selectivity and to inhibit not only cathepsin K but also other cysteine proteases strongly (see Non Patent Literatures 8 to 10).

As cathepsin K has attracted attention as mentioned above, studies such as X-ray crystallography of cathepsin K and inhibitors have been actively conducted (see Non Patent Literatures 6 and 11), and some compounds are currently known to have the effect of selectively inhibiting cathepsin K (see Patent Literatures 1 to 4 and Non Patent Literatures 12 to 15).

Cytochrome P450 (hereinafter also referred to as CYP) is a typical enzyme involved in drug metabolism. In particular, CYP3A4 is a molecular species involved in the metabolism of at least 50% of the drugs being clinically used at present. The presence of a drug capable of inhibiting a drug metabolism enzyme may incur the risk of causing or enhancing side effects by preventing the enzyme from metabolizing another drug used in combination and increasing the blood concentration of the drug used in combination (see Non Patent Literatures 16 and 17). At present, therefore, checking for CYP3A4 inhibitory activity is generally performed at the initial stage of drug development studies, and inhibitory compounds are generally excluded from candidate compounds (see Non Patent Literature 17). In particular, it is considered that drugs for treating osteoporosis must have low CYP3A4 inhibitory activity because elderly people, who are to be given the drugs, often take a combination of drugs and often have decreased drug metabolism.

$IC_{50}$ values (50% inhibitory concentrations) are generally used to determine the intensity of the CYP inhibitory activity. In general, the intensity is classified as a high level when $IC_{50}<1$ μM, a medium level when $1$ μM$<IC_{50}<10$ μM, and a low level when $IC_{50}>10$ μM (see Non Patent Literatures 18 and 19). Therefore, compounds with an $IC_{50}$ of more than 10 μM as the intensity of CYP3A4 inhibitory activity must be selected for drugs for chronic diseases of elderly people.

CITATION LIST

Patent Literatures

Patent Literature 1: JP 2000-204071 A
Patent Literature 2: WO 98/01133
Patent Literature 3: WO 01/58886
Patent Literature 4: WO 03/075836

Non Patent Literatures

Non Patent Literature 1: Biochem. Biophys. Res. Commun., 206, p 89 (1995)
Non Patent Literature 2: J. Biol. Chem., 271, p 12511 (1996)
Non Patent Literature 3: Science, 273, p 1236 (1996)
Non Patent Literature 4: J. Biol. Chem., 271, p 2126 (1996)
Non Patent Literature 5: Biol. Pharm. Bull., 19, p 1026 (1996)
Non Patent Literature 6: Nature Structural Biology, 4, p 105 (1997)
Non Patent Literature 7: J. Med. Chem., 38, p 3193 (1995)
Non Patent Literature 8: Enzyme Inhibition, 3, p 13 (1989)
Non Patent Literature 9: Biochem. Biophys. Res. Commun., 153, p 1201 (1988)

Non Patent Literature 10: J. Biochem., 88, p 1805 (1980)

Non Patent Literature 11: Nature Structural Biology, 4, p 109 (1997)

Non Patent Literature 12: Proc. Natl. Acad. Sci. USA., 94, p 14249 (1997)

Non Patent Literature 13: J. Am. Chem. Soc., 120, p 9114 (1998)

Non Patent Literature 14: J. Med. Chem., 41, p 3563 (1998)

Non Patent Literature 15: Bioorg. Med. Chem. Lett., 14, p 4897 (2004)

Non Patent Literature 16: Rinsho Yakubutsu Dotaigaku (Clinical Pharmacokinetics) (revised 4th edition), Nankodo Co., Ltd., p 71-85, p 173-228 (2009)

Non Patent Literature 17: Nichiyakurishi (Folia Pharmacol. Jpn.), 134, p 285-288 (2009)

Non Patent Literature 18: Phytomedicine. 2011 Apr. 15; 18(6): p 533-8

Non Patent Literature 19: Annu. Rev. Pharmacol. Toxicol. 2000; 40: p 133-57

SUMMARY OF INVENTION

Technical Problem

The present invention provides a novel compound that has cathepsin K inhibitory activity but has substantially no CYP3A4 inhibitory activity. More specifically, the present invention provides a bone resorption inhibitor having substantially no CYP3A4 inhibitory activity and a pharmaceutical composition useful for preventing and/or treating diseases caused by accelerated bone resorption, such as osteoporosis.

More specifically, the present invention provides a novel compound that has extremely low CYP3A4 inhibitory activity and is highly effective not only in inhibiting cathepsin K in vitro but also in inhibiting bone resorption in vivo; a bone resorption inhibitor including such a novel compound; and a pharmaceutical composition useful for preventing and/or treating diseases caused by accelerated bone resorption, such as osteoporosis.

Solution to Problem

So far, the inventors have developed a large number of cathepsin K-inhibiting compounds and tried to put them into practical use as drugs for treating metabolic bone diseases. Unfortunately, these compounds have been found to have high CYP3A4 inhibitory activity and have not been put into practical use yet. Thus, the inventors have actively searched for compounds that have cathepsin K inhibitory activity but have no CYP3A4 inhibitory activity. As a result, the inventors have surprisingly found that α-oxoacylaminocaprolactam derivatives, more specifically, compounds of formula (I) shown below exhibit almost no CYP3A4 inhibition and have high cathepsin K inhibitory activity, and have accomplished the present invention based on these findings.

Specifically, the present invention is directed to a novel α-oxoacylaminocaprolactam derivative and a pharmaceutical composition, specifically a bone resorption inhibitor, including the derivative as an active ingredient.

More specifically, the present invention is directed to items [1] to [14] below.

[1] An α-oxoacylaminocaprolactam derivative of formula (I):

[Chemical Formula 1]

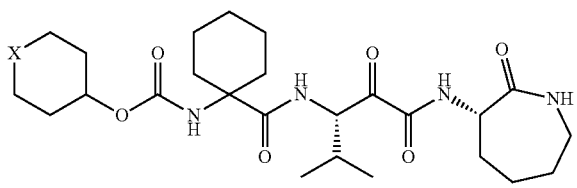

wherein X is —O— or —N(R$^1$)—, wherein R$^1$ is a (C1 to C10 alkoxy)carbonyl group.

[2] The α-oxoacylaminocaprolactam derivative according to item [1], wherein in formula (I), X is —O—.

[3] The α-oxoacylaminocaprolactam derivative according to item [1], wherein in formula (I), X is —N(R$^1$)—, wherein R$^1$ is a (C1 to C10 alkoxy)carbonyl group.

[4] The α-oxoacylaminocaprolactam derivative according to item [3], wherein R$^1$ is a methoxycarbonyl group.

[5] A bone resorption inhibitor including the α-oxoacylaminocaprolactam derivative according to any one of items [1] to [4].

[6] A pharmaceutical composition including the α-oxoacylaminocaprolactam derivative according to any one of items [1] to [4] and a pharmaceutically acceptable carrier.

[7] The pharmaceutical composition according to item [6], which is a medicament for treating or preventing a disease caused by accelerated bone resorption.

[8] The pharmaceutical composition according to item [7], wherein the disease caused by accelerated bone resorption is osteoporosis, hypercalcemia, Paget's disease, bone resorption disease, osteogenesis imperfecta, osteoarthritis, rheumatoid arthritis, arthritis, Klinefelter syndrome, hereditary hyperphosphatasia, Charcot neuroarthropathy, mastocytosis, Gaucher disease, cancer metastasis, or multiple myeloma.

[9] A method of treating a disease caused by accelerated bone resorption, including administering an effective amount of the α-oxoacylaminocaprolactam derivative according to any one of items [1] to [4] to a patient with a disease caused by accelerated bone resorption.

[10] The method according to item [9], wherein the disease caused by accelerated bone resorption is osteoporosis, hypercalcemia, Paget's disease, bone resorption disease, osteogenesis imperfecta, osteoarthritis, rheumatoid arthritis, arthritis, Klinefelter syndrome, hereditary hyperphosphatasia, Charcot neuroarthropathy, mastocytosis, Gaucher disease, cancer metastasis, or multiple myeloma.

[11] The α-oxoacylaminocaprolactam derivative according to any one of items [1] to [4], which is for use in a method of treating or preventing a disease caused by accelerated bone resorption.

[12] The α-oxoacylaminocaprolactam derivative according to item [11], wherein the disease caused by accelerated bone resorption is osteoporosis, hypercalcemia, Paget's disease, bone resorption disease, osteogenesis imperfecta, osteoarthritis, rheumatoid arthritis, arthritis, Klinefelter syndrome, hereditary hyperphosphatasia, Charcot neuroarthropathy, mastocytosis, Gaucher disease, cancer metastasis, or multiple myeloma.

[13] Use of the α-oxoacylaminocaprolactam derivative according any one of items [1] to [4] for the manufacture of a pharmaceutical composition for treating or preventing a disease caused by accelerated bone resorption.

[14] The use according to item [13], wherein the disease caused by accelerated bone resorption is osteoporosis, hypercalcemia, Paget's disease, bone resorption disease, osteogenesis imperfecta, osteoarthritis, rheumatoid arthritis, arthritis, Klinefelter syndrome, hereditary hyperphosphatasia, Charcot neuroarthropathy, mastocytosis, Gaucher disease, cancer metastasis, or multiple myeloma.

Advantageous Effects of Invention

The α-oxoacylaminocaprolactam derivative of formula (I) of the present invention, which has high cathepsin K inhibitory activity with only a low level of CYP3A4 inhibitory activity, can be used as an active ingredient in a pharmaceutical composition for preventing and/or treating diseases that can be ameliorated by inhibiting substantial bone resorption (such as osteoporosis, hypercalcemia, Paget's disease, bone resorption disease, osteogenesis imperfecta, osteoarthritis, rheumatoid arthritis, arthritis, Klinefelter syndrome, hereditary hyperphosphatasia, Charcot neuroarthropathy, mastocytosis, Gaucher disease, cancer metastasis, and multiple myeloma). The compound of the present invention has not only cathepsin K inhibitory activity in vitro but also high bone resorption inhibitory activity in vivo.

The α-oxoacylaminocaprolactam derivative of formula (I) of the present invention, which only has a low level of CYP3A4 inhibitory activity, is less likely to cause serious side-effects even when used in combination with other drugs. Therefore, the α-oxoacylaminocaprolactam derivative of formula (I) of the present invention can be safely administered to elderly people who suffer from different diseases and take many drugs in combination.

Therefore, the present invention provides a pharmaceutical composition for preventing and/or treating diseases caused by accelerated bone resorption, which includes, as an active ingredient, a safe, practical, orally-administrable compound that has bone resorption inhibitory activity and is less likely to cause serious side-effects even when used in combination with other drugs.

DESCRIPTION OF EMBODIMENTS

The α-oxoacylaminocaprolactam derivative of the present invention is a compound of formula (I) shown above. In each molecule of the compound of formula (I) of the present invention, any of the hydrogen atoms may be replaced by deuterium or tritium atoms.

The α-oxoacylaminocaprolactam derivative of formula (I) of the present invention is characterized in that it has a caprolactam (ε-lactam) group at the end, a nitrogen atom is bonded in the α-position relative to the caprolactam group, the steric configuration at the α-position is the S configuration, it has an isopropyl group at the center, the steric configuration of the carbon atom bonded to the isopropyl group is the S configuration, and it has a 1-amino-cyclohexanecarboxylic acid structure. The α-oxoacylaminocaprolactam derivative of formula (I) of the present invention is further characterized by having a saturated oxygen atom or a nitrogen atom-containing heterocyclic group, specifically, a tetrahydro-2H-pyran-4-yl group or a 1-(alkoxycarbonyl)-4-piperidinyl group, at the end.

The α-oxoacylaminocaprolactam derivative of the present invention is further characterized in that it has almost no CYP3A4 inhibitory activity but has high cathepsin K inhibitory activity, which is its specific property.

The α-oxoacylaminocaprolactam derivative of the present invention and the compound described in Patent Literature 1 are different compounds because the α-oxoacylaminocaprolactam derivative of the present invention differs in the $R^1$ moiety of the compound described in Patent Literature 1. Specifically, Patent Literature 1 states that $R^1$ may be a substituted amide group, and also states that the substituted amide group refers to a group represented by the formula $R^9$—CONH— and having any of various substituents on the carbon atom of the amide bond group, in which the substituent $R^9$ on the carbon atom may be the substituted or unsubstituted alkyl group, substituted alkoxy, phenoxy, 1-naphthyloxy, 2-naphthyloxy, substituted or unsubstituted alkenyl, substituted or unsubstituted amino, substituted or unsubstituted aromatic hydrocarbon, or substituted or unsubstituted heterocycle (Patent Literature 1, claim 6). In contrast, the α-oxoacylaminocaprolactam derivative of the present invention has a heterocycle-substituted oxy group (heterocyclyloxy group) in place of the $R^9$ substituent shown in Patent Literature 1. The compound of the present invention differs in this point from the compound described in Patent Literature 1.

In the α-oxoacylaminocaprolactam derivative of formula (I) of the present invention, the (C1 to C10 alkoxy)carbonyl group for $R^1$ is a group composed of an alkyl group and an oxycarbonyl group (—O—CO— group) bonded to the alkyl group, in which the alkyl group has 1 to 10 carbon atoms, preferably 1 to 6 carbon atoms, more preferably 1 to 4 carbon atoms. In the alkoxycarbonyl group, the total number of carbon atoms including the carbon atom of the carbonyl group is 2 to 11, preferably 2 to 7, more preferably 2 to 5. The (C1 to C10 alkoxy)carbonyl group may be, for example, methoxycarbonyl, ethoxycarbonyl, n-propoxycarbonyl, isopropoxycarbonyl, tert-butoxycarbonyl, or the like. The alkoxycarbonyl group is more preferably methoxycarbonyl.

The α-oxoacylaminocaprolactam derivative of formula (I) of the present invention may be the following:
[1-[[[(1S)-3-[[(3S)-hexahydro-2-oxo-1H-azepin-3-yl]amino]-1-(1-methylethyl)-2,3-dioxopropyl]amino]carbonyl]cyclohexyl]carbamic acid tetrahydro-2H-pyran-4-yl ester;
[1-[[[(1S)-3-[[(3S)-hexahydro-2-oxo-1H-azepin-3-yl]amino]-1-(1-methylethyl)-2,3-dioxopropyl]amino]carbonyl]cyclohexyl]carbamic acid 1-(methoxycarbonyl)-4-piperidinyl ester; or the like.

The α-oxoacylaminocaprolactam derivative of formula (I) of the invention encompasses not only an α-oxoacylaminocaprolactam derivative of formula (I) but also a pharmaceutically acceptable salt thereof, any of various hydrates and solvates thereof, any of crystal polymorphisms thereof, a deuterated derivative thereof, a tritiated derivative thereof, or the like. When the oxygen atom- or nitrogen atom-containing heterocyclic moiety in formula (I) further has an asymmetric center atom, the α-oxoacylaminocaprolactam derivative of formula (I) also encompasses any stereoisomer thereof or a mixture of stereoisomers thereof.

Solvates of the α-oxoacylaminocaprolactam derivative of formula (I) include hydrates and various solvates (e.g., solvates with water or an alcohol such as ethanol).

The α-oxoacylaminocaprolactam derivative of formula (I) of the present invention can be produced by an appropriate combination of known chemical synthesis techniques.

For example, the α-oxoacylaminocaprolactam derivative of formula (I) can be produced by the method shown below or a method similar thereto.

[Chemical Formula 2]

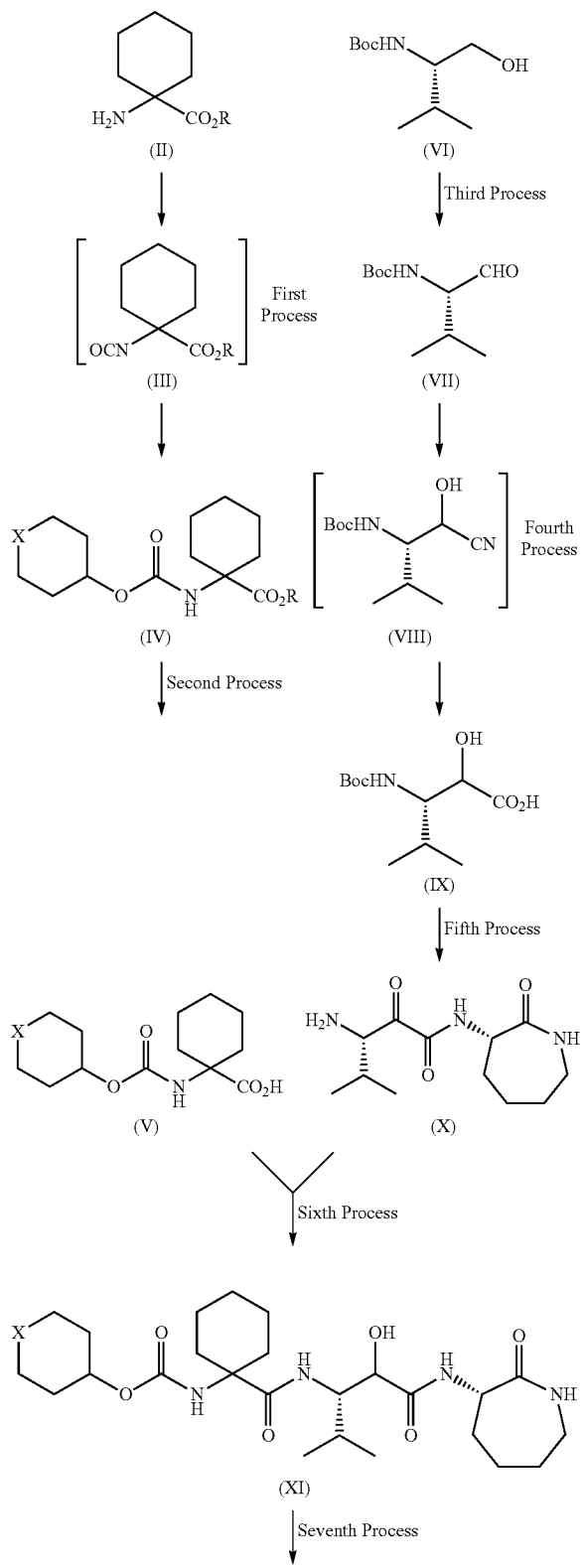

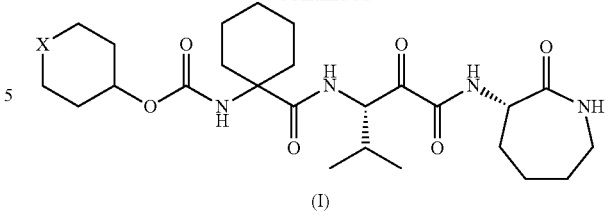

In the formulae, R is an ester residue, Boc is a tert-butoxycarbonyl group, and X is the same as defined above.

First Process

This process includes producing an isocyanate of formula (III) from an aminocyclohexanecarboxylic acid ester derivative of formula (II) and then allowing the isocyanate of formula (III) to react with an alcohol to produce an oxyamidocyclohexanecarboxylic acid ester derivative of formula (IV).

The process of producing the isocyanate (III) from the aminocyclohexanecarboxylic acid ester derivative of formula (II) may be performed by a technique using di-tert-butyl dicarbonate and 4-(dimethylamino)pyridine or a technique using phosgene or triphosgene. In this process, if necessary, a base may be added, such as pyridine, triethylamine, N,N-diisopropylethylamine, 4 (dimethylamino)pyridine, N-methylmorpholine, or N,N-dicyclohexylamine. This process is preferably performed in a solvent such as dichloromethane, chloroform, dichloroethane, ethyl acetate, acetone, benzene, toluene, xylene, dimethylformamide, acetonitrile, tetrahydrofuran, dioxane, diethyl ether, diisopropyl ether, or dimethoxyethane.

The reaction temperature is generally in the range of −30° C. to 200° C., preferably in the range of 0° to 100° C.

The process of producing the oxyamidocyclohexanecarboxylic acid ester derivative of formula (IV) by reaction of the isocyanate of formula (III) with an alcohol may be performed without any solvent or in a solvent. The solvent may be, for example, chloroform, dichloroethane, ethyl acetate, benzene, toluene, xylene, chlorobenzene, dichlorobenzene, dimethylformamide, acetonitrile, tetrahydrofuran, dioxane, or the like. In this process, a base may also be added, such as pyridine, triethylamine, N,N-diisopropylethylamine, 4-(dimethylamino)pyridine, N-methylmorpholine, or N,N-dicyclohexylamine. The base may be added in an amount in the range of a catalytic amount to an excess amount.

The reaction temperature may be in the range of 0° C. to 300° C., preferably in the range of 40° to 150° C.

The aminocyclohexanecarboxylic acid ester derivative of formula (II) may be a C1 to C6 linear or branched alkyl ester, preferably a C1 to C4 linear or branched alkyl ester; a C7 to C15 arylalkyl ester, preferably a C7 to C12 arylalkyl ester, or the like. Examples include 1-aminocyclohexanecarboxylic acid methyl ester, 1-aminocyclohexanecarboxylic acid ethyl ester, 1-aminocyclohexanecarboxylic acid n-propyl ester, 1-aminocyclohexanecarboxylic acid 2-propyl ester, 1-aminocyclohexanecarboxylic acid n-butyl ester, 1-aminocyclohexanecarboxylic acid 2-methylpropyl ester, 1-aminocyclohexanecarboxylic acid 1,1-dimethylethyl ester, 1-aminocyclohexanecarboxylic acid benzyl ester, and the like.

The alcohol to be allowed to react with the isocyanate of formula (III) may be, for example, tetrahydro-4-pyranol, 1-(alkoxycarbonyl)-4-hydroxypiperidine, preferably 1-tertbutoxycarbonyl-4-hydroxypiperidine, 1-methoxycarbonyl-4-hydroxypiperidine, or the like.

The oxyamidocyclohexanecarboxylic acid ester derivative of formula (IV) may be, for example, 1-[[[(tetrahydro-2H-pyran-4-yl)oxy]carbonyl]amino]cyclohexanecarboxylic acid methyl ester, 1-[[[(tetrahydro-2H-pyran-4-yl)oxy]carbonyl]amino]cyclohexanecarboxylic acid ethyl ester, 1-[[[(tetrahydro-2H-pyran-4-yl)oxy]carbonyl]amino]cyclohexanecarboxylic acid n-propyl ester, 1-[[[(tetrahydro-2H-pyran-4-yl)oxy]carbonyl]amino]cyclohexanecarboxylic acid 2-propyl ester, 1-[[[(tetrahydro-2H-pyran-4-yl)oxy]carbonyl]amino]cyclohexanecarboxylic acid n-butyl ester, 1-[[[(tetrahydro-2H-pyran-4-yl)oxy]carbonyl]amino]cyclohexanecarboxylic acid 2-methylpropyl ester, 1-[[[(tetrahydro-2H-pyran-4-yl)oxy]carbonyl]amino]cyclohexanecarboxylic acid 1,1-dimethylethyl ester, 1-[[[(tetrahydro-2H-pyran-4-yl)oxy]carbonyl]amino]cyclohexanecarboxylic acid benzyl ester; 1-[[[[1-[(1,1-dimethylethoxy)carbonyl]-4-piperidinyl]oxy]carbonyl]amino]cyclohexanecarboxylic acid methyl ester, 1-[[[[1-[(1,1-dimethylethoxy)carbonyl]-4-piperidinyl]oxy]carbonyl]amino]cyclohexanecarboxylic acid ethyl ester, 1-[[[[1-[(1,1-dimethylethoxy)carbonyl]-4-piperidinyl]oxy]carbonyl]amino]cyclohexanecarboxylic acid n-propyl ester, 1-[[[[1-[(1,1-dimethylethoxy)carbonyl]-4-piperidinyl]oxy]carbonyl]amino]cyclohexanecarboxylic acid 2-propyl ester, 1-[[[[1-[(1,1-dimethylethoxy)carbonyl]-4-piperidinyl]oxy]carbonyl]amino]cyclohexanecarboxylic acid n-butyl ester, 1-[[[[1-[(1,1-dimethylethoxy)carbonyl]-4-piperidinyl]oxy]carbonyl]amino]cyclohexanecarboxylic acid 2-methylpropyl ester, 1-[[[[1-[(1,1-dimethylethoxy)carbonyl]-4-piperidinyl]oxy]carbonyl]amino]cyclohexanecarboxylic acid 1,1-dimethylethyl ester, 1-[[[[1-[(1,1-dimethylethoxy)carbonyl]-4-piperidinyl]oxy]carbonyl]amino]cyclohexanecarboxylic acid benzyl ester; 1-[[[[1-(methoxycarbonyl)-4-piperidinyl]oxy]carbonyl]amino]cyclohexanecarboxylic acid methyl ester, 1-[[[[1-(methoxycarbonyl)-4-piperidinyl]oxy]carbonyl]amino]cyclohexanecarboxylic acid ethyl ester, 1-[[[[1-(methoxycarbonyl)-4-piperidinyl]oxy]carbonyl]amino]cyclohexanecarboxylic acid n-propyl ester, 1-[[[[1-(methoxycarbonyl)-4-piperidinyl]oxy]carbonyl]amino]cyclohexanecarboxylic acid 2-propyl ester, 1-[[[[1-(methoxycarbonyl)-4-piperidinyl]oxy]carbonyl]amino]cyclohexanecarboxylic acid n-butyl ester, 1-[[[[1-(methoxycarbonyl)-4-piperidinyl]oxy]carbonyl]amino]cyclohexanecarboxylic acid 2-methylpropyl ester, 1-[[[[1-(methoxycarbonyl)-4-piperidinyl]oxy]carbonyl]amino]cyclohexanecarboxylic acid 1,1-dimethylethyl ester, 1-[[[[1-(methoxycarbonyl)-4-piperidinyl]oxy]carbonyl]amino]cyclohexanecarboxylic acid benzyl ester; or the like.

Second Process

This process includes subjecting the oxyamidocyclohexanecarboxylic acid ester derivative of formula (IV) (produced in the first process) to a hydrolysis reaction or a hydrogenation reaction using a metal catalyst for catalytic reduction to produce an oxyamidocyclohexanecarboxylic acid of formula (V).

The hydrolysis reaction may be performed in the presence of an acid or a base. The acid may be, for example, hydrochloric acid, sulfuric acid, nitric acid, acetic acid, methanesulfonic acid, benzenesulfonic acid, p-toluenesulfonic acid, or the like. The base may be, for example, sodium hydroxide, potassium hydroxide, lithium hydroxide, sodium carbonate, potassium carbonate, or the like. This process is preferably performed in water or a mixed solvent of water and an organic solvent such as methanol, ethanol, 2-propanol, 1-butanol, 2-butanol, isobutanol, tetrahydrofuran, or dimethoxyethane. The reaction temperature is generally in the range of −20° C. to 200° C., preferably in the range of 0° to 180° C.

When the oxyamidocyclohexanecarboxylic acid ester derivative of formula (IV) is a benzyl ester (R is benzyl), the oxyamidocyclohexanecarboxylic acid of formula (V) can be produced by a hydrogenation reaction using a metal catalyst for catalytic reduction. The metal catalyst for the production by the catalytic hydrogenation reaction may be, for example, a platinum catalyst such as $PtO_2$ or Pt/C, a palladium catalyst such as Pd/C, $Pd/BaSO_4$, $Pd/CaCO_3$, $Pd/SrCO_3$, Pd black, PdO, or $Pd(OH)_2$, a nickel catalyst such as Raney nickel, a rhodium catalyst such as Rh/C, $Rh/Al_2O_3$, $RhCl\,(PPh_3)_3$, $RhH\,(CO)\,(PPh_3)_3$, or $Rh\,(OCOCH_3)_4$, a ruthenium catalyst such as $RuO_2$, Ru/C, $Ru(OCOMe)\,(PPh_3)_3$, or $Ru(OCOCF_3)(PPh_3)_3$, a copper catalyst such as Cu—CrO, Cu—Ba—CrO, or the like.

This process is preferably performed in a solvent such as methanol, ethanol, 2-propanol, 1-butanol, 2-butanol, isobutanol, diisopropyl ether, tetrahydrofuran, benzene, toluene, xylene, dimethylformamide, dioxane, or water. The reaction temperature is generally in the range of −50° C. to 200° C., preferably in the range of 10° to 100° C.

The oxyamidocyclohexanecarboxylic acid derivative of formula (V) may be, for example, 1-[[[(tetrahydro-2H-pyran-4-yl)oxy]carbonyl]amino]cyclohexanecarboxylic acid, 1-[[[[1-(methoxycarbonyl)-4-piperidinyl]oxy]carbonyl]amino]cyclohexanecarboxylic acid, 1-[[[[1-[(1,1-dimethylethoxy)carbonyl]-4-piperidinyl]oxy]carbonyl]amino]cyclohexanecarboxylic acid, or the like.

Third Process

This process includes oxidizing tert-butoxycarbonyl-L-valinol of formula (VI) to produce tert-butoxycarbonyl-L-valinal of formula (VII).

In this process, the oxidation reaction may be activated DMSO (dimethyl sulfoxide) oxidation. In this reaction, an electrophilic activating reagent may be used, such as dicyclohexylcarbodiimide, phosphorus pentoxide, a pyridine-sulfur trioxide complex, acetic anhydride, mercury(II) acetate, or oxalyl chloride. In this process, if necessary, a hydrogen donor may also be added, such as phosphoric acid, trifluoroacetic acid, dichloroacetic acid, pyridine-phosphoric acid, or pyridine-trifluoroacetic acid. If necessary, an amine may also be added, such as triethylamine, N,N-diisopropylethylamine, or N-methylmorpholine.

This process may be performed in dimethyl sulfoxide, and if necessary, a solvent may also be added, such as dichloromethane, chloroform, dichloroethane, toluene, acetone, or tetrahydrofuran.

The reaction temperature is generally in the range of −80° C. to 200° C., preferably in the range of −40° to 40° C.

Alternatively, in this process, an active species with a structure similar to that for the activated DMSO reaction may be prepared from a sulfide and a halogen for the oxidation reaction.

In this process, the sulfide may be, for example, dimethyl sulfide, methyl phenyl sulfide, or the like. The halogenating agent may be, for example, N-chlorosuccinimide, chlorine, or the like.

In this process, if necessary, an amine may also be added, such as triethylamine, N,N-diisopropylethylamine, N-methylmorpholine, or 1,8-diazabicyclo[5.4.0]undec-7-en (DBU).

This process is preferably performed in a solvent such as dichloromethane, chloroform, dichloroethane, toluene, or tetrahydrofuran.

The reaction temperature is generally in the range of −80° C. to 200° C., preferably in the range of −40° to 40° C.

Alternatively, in this process, the oxidation may be performed using a high-valence iodine compound reagent.

In this process, the high-valence iodine compound may be, for example, a Dess-Martin reagent (1,1,1-tris(acetoxy)-1,1-dihydro-1,2-benziodoxol-3-(1H)-one), IBX (1-hydroxy-1,2-benziodoxol-3-(1H)-1-oxide), or the like.

In this process, if necessary, a base may also be added, such as pyridine or sodium hydrogen carbonate.

This process is preferably performed in a solvent such as dichloromethane, chloroform, dichloroethane, benzene, toluene, xylene, dimethylformamide, acetonitrile, tetrahydrofuran, dioxane, or dimethoxyethane.

The reaction temperature may be in the range of −20° C. to 200° C., preferably in the range of 0° to 40° C.

Alternatively, in this process, the oxidation may be performed using an aluminum alkoxide and a hydrogen acceptor (Oppenauer oxidation). The aluminum alkoxide may be, for example, aluminum isopropoxide or aluminum tert-butoxide.

The hydrogen acceptor may be, for example, benzoquinone, benzophenone, acetone, cyclohexanone, benzaldehyde, or the like.

This process is preferably performed in a solvent such as benzene, toluene, or xylene.

The reaction temperature may be in the range of −20° C. to 200° C., preferably in the range of 0° to 150° C.

Alternatively, in this process, the oxidation reaction may be performed using tetrapropylammonium perruthenate (TPAP). N-methylmorpholine-N-oxide or molecular oxygen may be used as an oxidizing agent.

This process is preferably performed in a solvent such as dichloromethane, acetonitrile, or toluene. In this process, if necessary, molecular sieves 4A may be added.

The reaction temperature may be in the range of −20° C. to 200° C., preferably in the range of 0° to 40° C.

Alternatively, in this process, the oxidation reaction may be performed using 2,2,6,6-tetramethyl-1-piperidinyloxy radical (TEMPO) or a derivative thereof.

A hypochlorite is preferably used as an oxidizing agent. A bromite, N-chlorosuccinimide, or the like may also be used as an oxidizing agent.

This process is preferably performed in a solvent such as dimethyl sulfoxide, dimethylformamide, dichloromethane, acetonitrile, toluene, or ethyl acetate.

In this process, if necessary, sodium bromide or water may also be added.

The reaction temperature may be in the range of −20° C. to 200° C., preferably in the range of 0° to 40° C.

Fourth Process

This process includes adding a cyano group to the tert-butoxycarbonyl-L-valinal of formula (VII) to produce a cyanohydrin of formula (VIII), then subjecting the cyanohydrin of formula (VIII) to a hydrolysis reaction, and performing tert-butoxycarbonylation again to produce a hydroxycarboxylic acid of formula (IX).

In this process, the reaction to produce the cyanohydrin of formula (VIII) from the tert-butoxycarbonyl-L-valinal of formula (VII) may be performed using acetone cyanhydrin, sodium cyanide, potassium cyanide, hydrogen cyanide, copper cyanide, trimethylsilyl cyanide, or the like. If necessary, a base may also be added, such as pyridine, triethylamine, N,N-diisopropylethylamine, 4-(dimethylamino)pyridine, N-methylmorpholine, or N,N-dicyclohexylamine, or a Lewis acid may also be added, such as zinc chloride, titanium tetrachloride, titanium tetraisopropoxide, aluminum chloride, or zinc trifluoromethanesulfonate.

This process is preferably performed in a solvent such as dichloromethane, chloroform, dichloroethane, ethyl acetate, benzene, toluene, xylene, chlorobenzene, dichlorobenzene, dimethylformamide, acetonitrile, tetrahydrofuran, or dioxane.

The reaction temperature may be in the range of −20° C. to 200° C., preferably in the range of 0° to 100° C.

In this process, the cyanohydrin of formula (VIII) may be subjected to an acid hydrolysis reaction using an acid such as hydrochloric acid, sulfuric acid, nitric acid, acetic acid, methanesulfonic acid, benzenesulfonic acid, or p-toluenesulfonic acid. This reaction is preferably performed in water or a mixed solvent of water and an organic solvent such as methanol, ethanol, 2-propanol, 1-butanol, 2-butanol, isobutanol, tetrahydrofuran, dioxane, or dimethoxyethane. The reaction temperature is generally in the range of −20° C. to 200° C., preferably in the range of 0° to 180° C.

In the acid hydrolysis reaction, the Boc group for the amino group can also be decomposed simultaneously. To protect the amino group, therefore, tert-butoxycarbonylation reaction is preferably performed.

In this process, the tert-butoxycarbonylation reaction may be performed again using di-tert-butyl dicarbonate, 2-(tert-butoxycarbonylthio)-4,6-dimethylpyrimidine, or the like. The reaction may be performed in the presence of a base. The base may be an organic base such as pyridine, triethylamine, N,N-diisopropylethylamine, 4-(dimethylamino)pyridine, N-methylmorpholine, or N,N-dicyclohexylamine, or an inorganic base such as sodium hydroxide, potassium hydroxide, lithium hydroxide, sodium hydrogen carbonate, sodium carbonate, or potassium carbonate. This process is preferably performed in water or a mixed solvent of water and an organic solvent such as methanol, ethanol, 2-propanol, 1-butanol, 2-butanol, isobutanol, tetrahydrofuran, dioxane, ethyl acetate, diethyl ether, diisopropyl ether, or dimethoxyethane. The reaction temperature is generally in the range of −20° C. to 200° C., preferably in the range of −10° to 100° C.

Fifth Process

This process includes condensing the hydroxycarboxylic acid of formula (IX) with L-(−)-α-amino-ε-caprolactam, preferably in the presence of a condensing agent, and then deprotecting the product to produce an aminoalcohol of formula (X).

The condensing agent for use in this process may be, for example, dicyclohexylcarbodiimide, 1-ethyl-3-(3-dimethylaminopropyl)carbodiimide hydrochloride, diisopropylcarbodiimide, carbonyldiimidazole, 4-(4,6-dimethoxy-1,3,5-triazin-2-yl)-4-methylmorpholinium chloride n-hydrate (DMT-MM), 2-chloro-1-methylpyridinium iodide, or the like. In this process, if necessary, an activating agent may also be added, such as 1-hydroxybenzotriazole or N-hydroxysuccinimide.

Alternatively, in this process, the condensation may be performed by a mixed acid anhydride method using an acid halide in the presence of a base. The acid halide for use in this process may be, for example, pivaloyl chloride, isobutyl chloroformate, methyl chloroformate, ethyl chloroformate, methanesulfonyl chloride, benzenesulfonyl chloride, toluenesulfonyl chloride, or the like. The base may be, for example, pyridine, triethylamine, N,N-diisopropylethylamine, 4-(dimethylamino)pyridine, N-methylmorpholine, N,N-dicyclohexylamine, or the like.

This process is preferably performed in a solvent such as dichloromethane, chloroform, dichloroethane, ethyl acetate, acetone, benzene, toluene, xylene, dimethylformamide, acetonitrile, tetrahydrofuran, dioxane, diethyl ether, diisopropyl ether, or dimethoxyethane.

The reaction temperature is generally in the range of −30° C. to 200° C., preferably in the range of −10° to 100° C.

The subsequent deprotection reaction may be performed using an acid such as hydrogen chloride, hydrochloric acid, sulfuric acid, nitric acid, acetic acid, methanesulfonic acid, benzenesulfonic acid, or p-toluenesulfonic acid. This reaction is preferably performed in a solvent such as methanol, ethanol, 2-propanol, 1-butanol, 2-butanol, isobutanol, tetrahydrofuran, dioxane, ethyl acetate, or dimethoxyethane.

Sixth Process

This process includes condensing the oxyamidocyclohexanecarboxylic acid of formula (V) with the aminoalcohol of formula (X), preferably in the presence of a condensing agent, to produce an α-hydroxyacylaminocaprolactam of formula (XI).

The condensing agent for use in this process may be, for example, dicyclohexylcarbodiimide, 1-ethyl-3-(3-dimethylaminopropyl)carbodiimide hydrochloride, diisopropylcarbodiimide, carbonyldiimidazole, 4-(4,6-dimethoxy-1,3,5-triazin-2-yl)-4-methylmorpholinium chloride n-hydrate (DMT-MM), 2-chloro-1-methylpyridinium iodide, or the like. In this process, if necessary, an activating agent may also be added, such as 1-hydroxybenzotriazole or N-hydroxysuccinimide.

Alternatively, in this process, the condensation may be performed by a mixed acid anhydride method using an acid halide in the presence of a base. The acid halide for use in this process may be, for example, pivaloyl chloride, isobutyl chloroformate, methyl chloroformate, ethyl chloroformate, methanesulfonyl chloride, benzenesulfonyl chloride, toluenesulfonyl chloride, or the like. The base may be, for example, pyridine, triethylamine, N,N-diisopropylethylamine, 4-(dimethylamino)pyridine, N-methylmorpholine, N,N-dicyclohexylamine, or the like.

This process is preferably performed in a solvent such as dichloromethane, chloroform, dichloroethane, ethyl acetate, acetone, benzene, toluene, xylene, dimethylformamide, acetonitrile, tetrahydrofuran, dioxane, diethyl ether, diisopropyl ether, or dimethoxyethane.

The reaction temperature is generally in the range of −30° C. to 200° C., preferably in the range of −10° to 100° C.

Seventh Process

This process includes oxidizing the α-hydroxyacylaminocaprolactam of formula (XI) to produce the α-oxyacylaminocaprolactam of formula (I).

In this process, the oxidation reaction may be activated DMSO (dimethyl sulfoxide) oxidation. In this reaction, an electrophilic activating reagent may be used, such as dicyclohexylcarbodiimide, phosphorus pentoxide, a pyridine-sulfur trioxide complex, acetic anhydride, mercury(II) acetate, or oxalyl chloride. In this process, if necessary, a hydrogen donor may also be added, such as phosphoric acid, trifluoroacetic acid, dichloroacetic acid, pyridine-phosphoric acid, or pyridine-trifluoroacetic acid. If necessary, an amine may also be added, such as triethylamine, N,N-diisopropylethylamine, or N-methylmorpholine.

This process may be performed in dimethyl sulfoxide, and if necessary, a solvent may be added, such as dichloromethane, chloroform, dichloroethane, toluene, acetone, or tetrahydrofuran.

The reaction temperature is generally in the range of −80° C. to 200° C., preferably in the range of −40° to 40° C.

Alternatively, in this process, an active species with a structure similar to that for the activated DMSO reaction may be prepared from a sulfide and a halogen for the oxidation reaction.

In this process, the sulfide may be, for example, dimethyl sulfide, methyl phenyl sulfide, or the like. The halogenating agent may be, for example, N-chlorosuccinimide, chlorine, or the like.

In this process, if necessary, an amine may also be added, such as triethylamine, N,N-diisopropylethylamine, N-methylmorpholine, or 1,8-diazabicyclo[5.4.0]undec-7-en (DBU).

This process is preferably performed in a solvent such as dichloromethane, chloroform, dichloroethane, toluene, or tetrahydrofuran.

The reaction temperature is generally in the range of −80° C. to 200° C., preferably in the range of −40° to 40° C.

Alternatively, in this process, the oxidation may be performed using a high-valence iodine compound reagent.

In this process, the high-valence iodine compound may be, for example, a Dess-Martin reagent (1,1,1-tris(acetoxy)-1,1-dihydro-1,2-benziodoxol-3-(1H)-one), IBX (1-hydroxy-1,2-benziodoxol-3-(1H)-1-oxide), or the like.

In this process, if necessary, a base may also be added, such as pyridine or sodium hydrogen carbonate.

This process is preferably performed in a solvent such as dichloromethane, chloroform, dichloroethane, benzene, toluene, xylene, dimethylformamide, acetonitrile, tetrahydrofuran, dioxane, or dimethoxyethane.

The reaction temperature may be in the range of −20° C. to 200° C., preferably in the range of 0° to 40° C.

Alternatively, in this process, the oxidation may be performed using an aluminum alkoxide and a hydrogen acceptor (Oppenauer oxidation). The aluminum alkoxide may be, for example, aluminum isopropoxide or aluminum tert-butoxide.

The hydrogen acceptor may be, for example, benzoquinone, benzophenone, acetone, cyclohexanone, benzaldehyde, or the like.

This process is preferably performed in a solvent such as benzene, toluene, or xylene.

The reaction temperature may be in the range of −20° C. to 200° C., preferably in the range of 0° to 150° C.

Alternatively, in this process, the oxidation reaction may be performed using tetrapropylammonium perruthenate (TPAP). N-methylmorpholine-N-oxide or molecular oxygen may be used as an oxidizing agent.

This process is preferably performed in a solvent such as dichloromethane, acetonitrile, or toluene. In this process, if necessary, molecular sieves 4A may be added.

The reaction temperature may be in the range of −20° C. to 200° C., preferably in the range of 0° to 40° C.

Alternatively, in this process, the oxidation reaction may be performed using 2,2,6,6-tetramethyl-1-piperidinyloxy radical (TEMPO) or a derivative thereof.

A hypochlorite is preferably used as an oxidizing agent. A bromite, N-chlorosuccinimide, or the like may also be used as an oxidizing agent.

This process is preferably performed in a solvent such as dimethyl sulfoxide, dimethylformamide, dichloromethane, acetonitrile, toluene, or ethyl acetate. In this process, if necessary, sodium bromide or water may also be added.

The reaction temperature may be in the range of −20° C. to 200° C., preferably in the range of 0° to 40° C.

If necessary, the intermediates and the α-oxoacylaminocaprolactam derivative of formula (I) of the present invention, produced by any of these processes, may be purified by any of various known purification methods such as recrystallization, distillation, and chromatography. If necessary, optical resolution may also be performed by any of various known methods.

The test results described below show that in the evaluation of cathepsin K inhibitory activity and the evaluation of bone resorption inhibitory activity using male mice, the α-oxoacylaminocaprolactam derivative of formula (I) of the present invention has activity equal to or greater than that of the compounds (cyclic amides) in the group described in JP 2000-204071 A, which are known to have cathepsin K inhibitory activity. However, the compounds (cyclic amides) in the group described in JP 2000-204071 A have CYP3A4 inhibitory activity and cannot only have bone resorption inhibitory activity without CYP3A4 inhibitory activity.

In contrast, compounds according to the present invention all have bone resorption inhibitory activity with no CYP3A4 inhibitory activity, which means that the compound group of the present invention can only have the desired pharmacological activity without any CYP3A4 inhibitory activity which may cause side effects.

Although it is not clear why the compound of the present invention has bone resorption inhibitory activity with no CYP3A4 inhibitory activity, it is suggested that only compounds with an extremely limited structure can be free of CYP3A4 inhibitory activity.

As shown below, the compound of the present invention has selective and potent cathepsin K inhibitory activity and high bone resorption inhibitory activity in an animal model. In addition, the compound of the present invention can serve as a bone resorption inhibitor with less side effects even when used in combination with other drugs. Therefore, the compound of the present invention can be used as an active ingredient in pharmaceutical compositions for treating or preventing diseases caused by accelerated bone resorption. Diseases caused by accelerated bone resorption include osteoporosis, hypercalcemia, Paget's disease, bone resorption diseases, osteogenesis imperfecta, osteoarthritis, rheumatoid arthritis, arthritis, Klinefelter syndrome, hereditary hyperphosphatasia, Charcot neuroarthropathy, mastocytosis, Gaucher disease, cancer metastasis, multiple myeloma, and the like.

The bone resorption inhibitor of the present invention or the therapeutic agent of the present invention for diseases caused by accelerated bone resorption includes the α-oxoacylaminocaprolactam derivative of formula (I) as an active ingredient and can be used as a pharmaceutical composition containing the active ingredient. In this case, the compound of the present invention is generally used together with a pharmaceutically acceptable carrier and/or diluent, although the compound of the present invention may be used alone.

The compound of the present invention may be administered by any method. A suitable preparation for the compound of the present invention may be selected as appropriate depending on the therapeutic purpose. For example, such a preparation may be any of an oral agent, an injection, a suppository, an inhalant, and the like. Pharmaceutical compositions suitable for these dosage forms can be produced using known preparation methods.

For example, when oral solid preparations are prepared, the compound of formula (I) may be mixed with a pharmaceutically acceptable excipient and optionally an additive such as a binder, a disintegrator, a lubricant, a colorant, a corrigent, or a flavoring agent, and then tablets, coated tables, granules, powders, capsules, or the like may be prepared from the mixture using conventional methods. The additives may be appropriately selected from those generally used in the art. Examples of the excipient include lactose, sucrose, sodium chloride, glucose, starch, calcium carbonate, kaolin, microcrystalline cellulose, silicate, and the like.

Examples of the binder include water, ethanol, propanol, simple syrup, glucose solutions, starch solutions, gelatin solutions, carboxymethyl cellulose, hydroxypropyl cellulose, hydroxypropyl starch, methyl cellulose, ethyl cellulose, shellac, calcium phosphate, polyvinylpyrrolidone, and the like. Examples of the disintegrator include dry starch, sodium alginate, agar powder, sodium hydrogen carbonate, calcium carbonate, sodium lauryl sulfate, stearic acid monoglyceride, lactose, and the like. Examples of the lubricant include purified talc, stearates, borax, polyethylene glycol, and the like. Examples of the corrigent include sucrose, bitter orange peel, citric acid, tartaric acid, and the like.

When an oral liquid preparation is prepared, internal liquid, syrup, elixir, or the like may be prepared by mixing the compound of formula (I) with a corrigent, a buffer, a stabilizer, a flavoring agent, and the like using conventional methods. The corrigent may be any of those listed above. The buffer may be sodium citrate or the like, and the stabilizer may be gum tragacanth, gum arabic, gelatin, or the like.

When an injection is prepared, a hypodermic injection, an intramuscular injection, and an intravenous injection may be prepared by mixing the compound of formula (I) with a pH adjusting agent, a buffer, a stabilizer, an isotonizing agent, a local anesthetic, and the like using conventional methods. Example of the pH adjusting agent and the buffer include sodium citrate, sodium acetate, sodium phosphate, and the like. Examples of the stabilizer include sodium pyrosulfite, EDTA, thioglycolic acid, thiolactic acid, and the like. Examples of the local anesthetic include procaine hydrochloride, lidocaine hydrochloride, and the like. Examples of the isotonizing agent include sodium chloride, glucose, and the like.

A suppository can be prepared by mixing the compound of formula (I) with a known suppository carrier, such as polyethylene glycol, lanolin, cacao butter, or fatty acid triglyceride, and optionally a surfactant (such as Tween (registered trademark)) and then forming the suppository using conventional methods.

Besides those listed above, other preferred preparations may be appropriately prepared using conventional methods.

In general, 1 mg to 1,000 mg of the compound of formula (I) is preferably administered to an adult orally or parenterally once or in several divided doses per day, although the dosage of the compound of formula (I) depends on the age, weight, and condition of the subject, dosage form, dosage frequency, and the like.

Hereinafter, the present invention will be more specifically described with reference to examples. It will be understood that the production examples and the examples are not intended to limit the present invention at all.

EXAMPLES

Production Example 1

Production of 1-[[[(tetrahydro-2H-pyran-4-yl)oxy]carbonyl]amino]cyclohexanecarboxylic acid

[Chemical Formula 3]

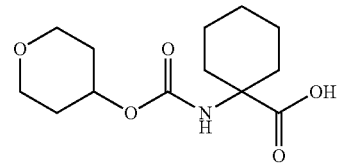

17

(1) Production of 1-[[[(tetrahydro-2H-pyran-4-yl)oxy]carbonyl]amino]cyclohexanecarboxylic acid benzyl ester

[Chemical Formula 4]

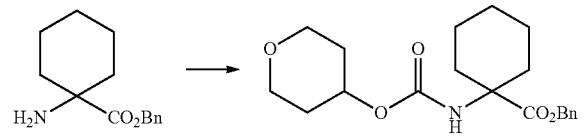

Benzyl 1-aminocyclohexanecarboxylate (11.1 g, 50 mmol) was added to a dichloromethane solution of di-tert-butyl dicarbonate (10.9 g, 50 mmol) and 4-dimethylaminopyridine (622 mg, 5 mmol) and stirred at room temperature for 30 minutes. The reaction mixture was concentrated in vacuo. Tetrahydro-4-pyranol (6.13 g, 60 mmol) and N,N-diisopropylethylamine (7.75 g, 60 mmol) were added to the residue and stirred at 100° C. for 12 hours. The reaction mixture was returned to room temperature and diluted with 20% ethyl acetate/hexane. The dilution was then washed once with a 10% potassium hydrogen sulfate aqueous solution and twice with water. After the organic layer was dried over anhydrous sodium sulfate, the solvent was removed by distillation in vacuo, so that 15.87 g (88%) of the title compound was obtained.

$^1$H-NMR (CDCl$_3$, δ):
1.22-1.36 (1H, m), 1.40-1.68 (7H, m), 1.81-1.90 (4H, m), 1.95-2.09 (2H, m), 3.47 (2H, td, J=10 Hz, 3 Hz), 3.85 (2H, br-s), 4.71-4.80 (1H, m), 4.87 (1H, br-s), 5.14 (2H, s), 7.26-7.36 (5H, m)

(2) Production of 1-[[[(tetrahydro-2H-pyran-4-yl)oxy]carbonyl]amino]cyclohexanecarboxylic acid

[Chemical Formula 5]

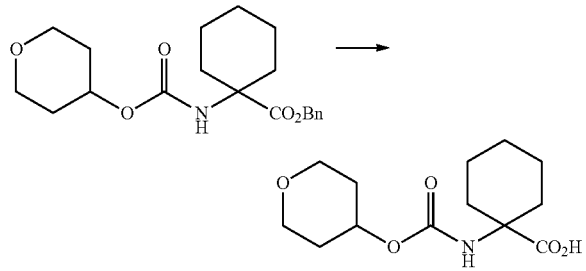

To a methanol solution of 1-[[[(tetrahydro-2H-pyran-4-yl)oxy]carbonyl]amino]cyclohexanecarboxylic acid benzyl ester (15.87 g, 43.9 mmol) was added 10% palladium-carbon (1.59 g) and stirred at room temperature under a hydrogen gas atmosphere overnight. The insoluble matter was removed by filtration, and the filtrate was concentrated in vacuo. Diisopropyl ether was added to the residue, and the resulting suspension was stirred overnight. The resulting crystals were separated by filtration and dried in vacuo to give 10.83 g (91%) of the title compound.

$^1$H-NMR (CDCl$_3$, δ):
1.25-1.38 (1H, m), 1.39-1.52 (3H, m), 1.59-1.72 (4H, m), 1.80-2.11 (6H, m), 3.45-3.60 (2H, m), 3.90 (2H, br-s), 4.85 (1H, br-s), 4.92 (1H, br-s)

18

Production Example 2

Production of (2R,3S)-3-amino-N-[(3S)-hexahydro-2-oxo-1H-azepin-3-yl]-2-hydroxy-4-methylpentanamide and (2S,3S)-3-amino-N-[(3S)-hexahydro-2-oxo-1H-azepin-3-yl]-2-hydroxy-4-methylpentanamide

[Chemical Formula 6]

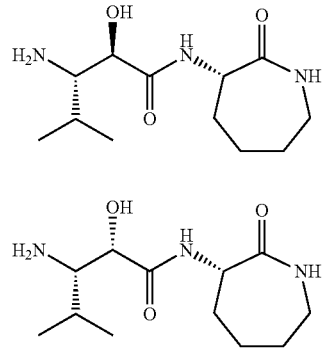

(1) Production of Boc-L-valinal

[Chemical Formula 7]

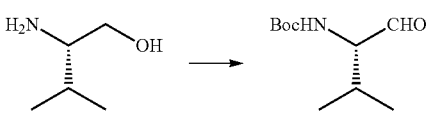

Di-tert-butyl dicarbonate (211.6 g, 0.97 mol) was gradually added to a dichloromethane solution of L-valinol (100.0 g, 0.97 mol). The reaction mixture was stirred at room temperature overnight and then concentrated in vacuo. To the residue (crude Boc-L-valinol) were added N,N-diisopropylethylamine (51.7 g, 0.4 mol), 1 L of dry dimethyl sulfoxide, and 200 ml of dry dichloromethane. Under ice cooling, sulfur trioxide-pyridine (63.7 g, 0.4 mol) was gradually added to the liquid mixture and stirred at the same temperature for 1 hour. The reaction mixture was poured into ice-water and then extracted twice with ethyl acetate. The organic layer was washed with a 20% citric acid aqueous solution, a saturated sodium hydrogen carbonate aqueous solution, and brine. After the organic layer wad dried over anhydrous sodium sulfate, the solvent was removed by distillation in vacuo, so that 179.3 g (92%) of the title compounds were obtained.

$^1$H-NMR (CDCl$_3$, δ):
0.95 (3H, d, J=7 Hz), 1.04 (3H, d, J=7 Hz), 1.45 (9H, m), 2.24-2.34 (1H, m), 4.22-4.28 (1H, m), 5.08 (1H, br-s), 9.65 (1H, s)

(2) Production of (2RS,3S)-2-hydroxy-4-methyl-3-[[(1,1-dimethylethoxy)carbonyl]amino]pentanoic acid

[Chemical Formula 8]

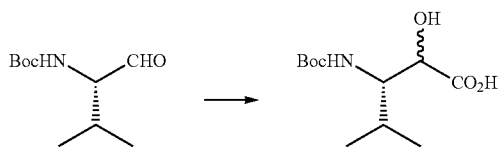

Under ice cooling, triethylamine (9.0 g, 89 mmol) was added dropwise to a dichloromethane solution of Boc-L-valinal (179.3 g, 881 mmol) and acetone cyanhydrin (310.6 g, 3.56 mol). The reaction mixture was returned to room temperature and then stirred overnight. The reaction mixture was concentrated in vacuo, and the residue was dissolved in 20% ethyl acetate/hexane. The solution was washed with water. The aqueous layer was extracted with 20% ethyl acetate/hexane, and the extract was combined with the organic layer. The organic layer was further washed with water, and the aqueous layer was again extracted with 20% ethyl acetate/hexane, and the extract was combined with the organic layer. After the combined organic layer was dried over anhydrous sodium sulfate, the solvent was removed by distillation in vacuo. The residue (crude (2RS,3S)-2-hydroxy-4-methyl-3-[[(1,1-dimethylethoxy)carbonyl]amino]pentanenitrile) was dissolved in 500 ml of dioxane, and 500 ml of concentrated hydrochloric acid was added dropwise to the solution. The liquid mixture was refluxed for 2 hours and then returned to room temperature. The solvent was then removed by distillation in vacuo. After the residue was dissolved in water, 300 ml of triethylamine was added to the solution. The mixture was stirred at room temperature for 1 hour and then concentrated again in vacuo. The residue was dissolved in 400 ml of dioxane and 400 ml of water. After triethylamine (108.3 g, 1.07 mol) was added to the solution, di-tert-butyl dicarbonate (194.2 g, 0.89 mol) was added to the mixture and then stirred at room temperature overnight. The reaction mixture was concentrated. After the concentrate was dissolved in diethyl ether, the solution was extracted once with water and twice with 90 ml of a 1 M sodium hydroxide aqueous solution. Under ice cooling, 15 ml of concentrated hydrochloric acid was added to the combined aqueous layer. After returned to room temperature, the liquid mixture was acidified with potassium hydrogen sulfate and then extracted twice with ethyl acetate. After the organic layer was dried over anhydrous sodium sulfate, the solvent was removed by distillation in vacuo, so that 141.0 g (64%) of the title compound was obtained.

$^1$H-NMR (CDCl$_3$, δ):

0.99 (3H, d, J=7 Hz), 1.05 (3H, d, J=7 Hz), 1.42 (9/2H, s), 1.45 (9/2H, s), 2.01-2.16 (1H, m), 3.55-3.68 (1H, m), 4.39 (1/2H, d, J=2 Hz), 4.41 (1/2H, d, J=3 Hz), 4.86 (1/2H, d, J=7 Hz), 4.99 (1/2H, d, J=10 Hz)

(3) Production of (2R,3S)-N-[(3S)-hexahydro-2-oxo-1H-azepin-3-yl]-2-hydroxy-4-methyl-3-[[(1,1-dimethylethoxy) carbonyl]amino]pentanamide and (4) production of (2S,3S)-N-[(3S)-hexahydro-2-oxo-1H-azepin-3-yl]-2-hydroxy-4-methyl-3-[[(1,1-dimethylethoxy)carbonyl]amino]pentanamide

[Chemical Formula 9]

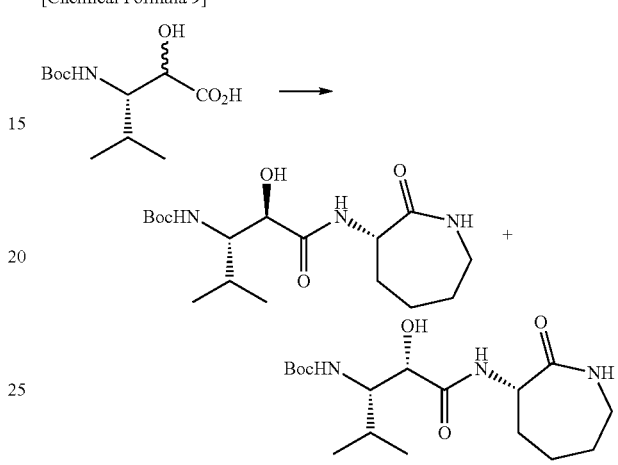

Under ice cooling, 1-ethyl-3-(3-dimethylaminopropyl)carbodiimide hydrochloride (120.2 g, 0.63 mol) was added to an N,N-dimethylformamide solution of (2RS,3S)-2-hydroxy-4-methyl-3-[[(1,1-dimethylethoxy)carbonyl]amino]pentanoic acid (141.0 g, 0.57 mol), L-(−)-α-amino-ε-caprolactam (73.1 g, 0.57 mol), and 1-hydroxybenzotriazole (91.7 g, 0.60 mol). The reaction mixture was returned to room temperature, stirred overnight, and then poured into a 1:1 aqueous solution of a saturated sodium hydrogen carbonate aqueous solution and water. The precipitated crystals were separated by filtration and then washed with water. The filtrate was extracted with chloroform, and the organic layer was washed with a 10% potassium hydrogen sulfate aqueous solution, saturated sodium bicarbonate water, and brine, and then dried over sodium sulfate. The solvent was removed by distillation in vacuo. Ethyl acetate was added to the residue and stirred for 4 hours. The precipitated crystals were separated by filtration and combined with the previously obtained crystals. The combined crystals were dissolved in methanol-chloroform. After the solution was dried over anhydrous sodium sulfate, the solvent was removed by distillation in vacuo, so that 105.2 g (52%) of title compound (3) was obtained. After the filtrate was concentrated in vacuo, diisopropyl ether was added to the residue and stirred overnight. The precipitated crystals were separated by filtration to give 76.9 g (38%) of title compound (4).

(3) $^1$H-NMR (CDCl$_3$, δ):

0.98 (3H, d, J=7 Hz), 1.04 (3H, d, J=7 Hz), 1.35-1.59 (2H, m), 1.38 (9H, s), 1.70-1.87 (2H, m), 1.92-2.16 (3H, m), 3.20-3.33 (2H, m), 3.46 (1H, ddd, J=9 Hz, 9 Hz, 2 Hz), 4.33 (1H, d, J=2 Hz), 4.52-4.61 (2H, m), 4.94 (1H, d, J=9 Hz), 6.25 (1H, br-s), 7.58 (1H, d, J=6 Hz)

(4) $^1$H-NMR (CDCl$_3$, δ):

0.96 (3H, d, J=7 Hz), 1.02 (3H, d, J=7 Hz), 1.32-1.59 (2H, m), 1.44 (9H, s), 1.77-1.91 (2H, m), 1.99-2.20 (2H, m), 2.08-2.20 (1H, m), 3.21-3.34 (2H, m), 3.56 (1H, ddd, J=8 Hz, 8 Hz, 2 Hz), 4.29 (1H, dd, J=6 Hz, 2 Hz), 4.52 (1H, dd, J=11 Hz, 6 Hz), 4.75 (1H, d, J=6 Hz), 4.85 (1H, d, J=8 Hz), 6.06 (1H, br-s), 8.01 (1H, d, J=6 Hz)

(5) Production of (2R,3S)-3-amino-N-[(3S)-hexahydro-2-oxo-1H-azepin-3-yl]-2-hydroxy-4-methyl-pentanamide

[Chemical Formula 10]

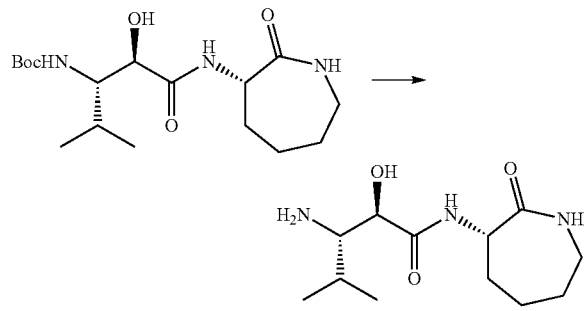

Four M hydrochloric acid/dioxane was added to (2R,3S)-N-[(3S)-hexahydro-2-oxo-1H-azepin-3-yl]-2-hydroxy-4-methyl-3-[[(1,1-dimethylethoxy)carbonyl]amino]pentanamide (105.2 g, 294 mmol) and allowed to stand at room temperature for 2 hours. The reaction mixture was concentrated in vacuo. After the residue was dissolved in water, the solution was allowed to pass through 180 ml of ion exchange resin (DOWEX, 1×4, 100-400 mesh). The eluate was concentrated in vacuo. The residue was dissolved in methanol-chloroform. After the solution was dried over anhydrous sodium sulfate, the solvent was removed by distillation in vacuo. Diisopropyl ether was added to the residue and stirred overnight. The precipitated crystals were separated by filtration to give 75.7 g (quantitative) of the title compound.

$^1$H-NMR (CDCl$_3$, δ):
1.01 (6H, d, J=7 Hz), 1.37-1.49 (1H, m), 1.56-1.68 (1H, m), 1.74-1.94 (3H, m), 1.99-2.09 (2H, m), 3.05 (1H, dd, J=7 Hz, 2 Hz), 3.22-3.37 (2H, m), 4.09 (1H, d, J=2 Hz), 4.57 (1H, dd, J=11 Hz, 7 Hz), 6.29 (1H, br-s), 7.82 (1H, d, J=7 Hz)

(6) Production of (2S,3S)-3-amino-N-[(3S)-hexahydro-2-oxo-1H-azepin-3-yl]-2-hydroxy-4-methyl-pentanamide

[Chemical Formula 11]

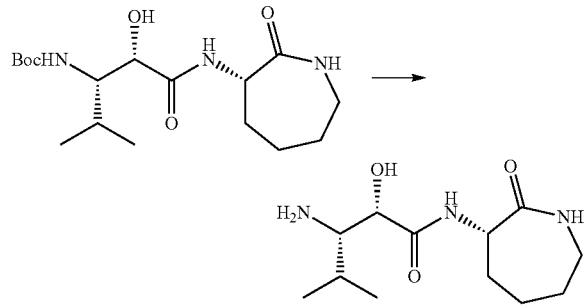

Using (2S,3S)-N-[(3S)-hexahydro-2-oxo-1H-azepin-3-yl]-2-hydroxy-4-methyl-3-[[(1,1-dimethylethoxy)carbonyl]amino]pentanamide (76.9 g, 215 mmol), the same procedure as in the production (5) was performed to produce 40.8 g (74%) of the title compound.

$^1$H-NMR (CDCl$_3$, δ):
0.88 (3H, d, J=7 Hz), 0.94 (3H, d, J=7 Hz), 1.32-1.47 (1H, m), 1.52-1.60 (1H, m), 1.77-1.89 (2H, m), 1.98-2.08 (2H, m), 2.14-2.32 (1H, m), 2.66 (1H, dd, J=9 Hz, 4 Hz), 3.29-3.35 (2H, m), 3.78 (1H, d, J=9 Hz), 4.60 (1H, ddd, J=11 Hz, 6 Hz, 1 Hz), 5.97 (1H, br-s), 9.32 (1H, d, J=6 Hz)

Production Example 3

Production of [1-[[[(1S,2R)-3-[[(3S)-hexahydro-2-oxo-1H-azepin-3-yl]amino]-2-hydroxy-1-(1-methylethyl)-3-oxopropyl]amino]carbonyl]cyclohexyl]carbamic acid tetrahydro-2H-pyran-4-yl ester

[Chemical Formula 12]

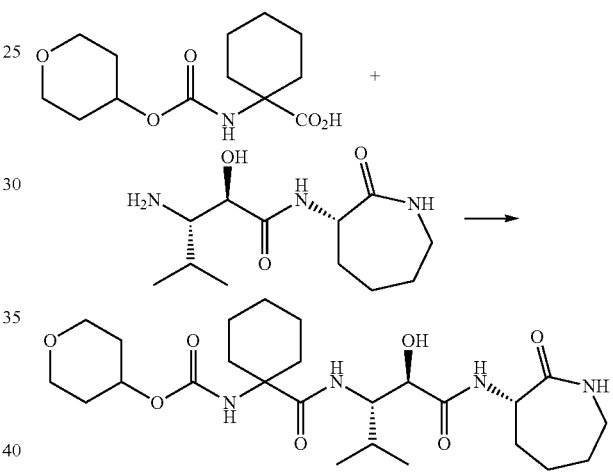

Under ice cooling, 1-ethyl-3-(3-dimethylaminopropyl)carbodiimide hydrochloride (49.2 g, 257 mmol) was added to a dichloromethane solution of 1-[[[(tetrahydro-2H-pyran-4-yl)oxy]carbonyl]amino]cyclohexanecarboxylic acid (63.3 g, 233 mmol), (2R,3S)-3-amino-N-[(3S)-hexahydro-2-oxo-1H-azepin-3-yl]-2-hydroxy-4-methylpentanamide (60.0 g, 233 mmol), 1-hydroxybenzotriazole (35.7 g, 245 mmol), and triethylamine (28.3 g, 280 mmol). The liquid mixture was returned to room temperature and stirred overnight. The reaction mixture was diluted with dichloromethane. The dilution was washed with a 10% potassium hydrogen sulfate aqueous solution, a saturated sodium hydrogen carbonate aqueous solution, and brine. After the organic layer was dried over anhydrous sodium sulfate, the solvent was removed by distillation in vacuo. Ethyl acetate was added to the residue and stirred overnight. The precipitated crystals were separated by filtration to give 107.4 g (90%) of the title compound.

$^1$H-NMR (CDCl$_3$, δ):
0.94 (3H, d, J=7 Hz), 1.03 (3H, d, J=7 Hz), 1.22-2.04 (20H, m), 2.19-2.31 (1H, m), 3.19-3.33 (2H, m), 3.51 (2H, td, J=12 Hz, 3 Hz), 3.62-3.69 (1H, m), 3.92 (2H, dt, J=12 Hz, 4 Hz), 4.31 (1H, dd, J=6 Hz, 3 Hz), 4.52 (1H, dd, J=11 Hz, 7 Hz), 4.75-4.83 (1H, m), 4.93 (1H, s), 5.15 (1H, d, J=6 Hz), 6.10 (1H, br-s), 7.09 (1H, d, J=7 Hz), 7.71 (1H, d, J=6 Hz)

Production Example 4

Production of [1-[[[(1S,2S)-3-[[(3S)-hexahydro-2-oxo-1H-azepin-3-yl]amino]-2-hydroxy-1-(1-methylethyl)-3-oxopropyl]amino]carbonyl]cyclohexyl]carbamic acid tetrahydro-2H-pyran-4-yl ester

[Chemical Formula 13]

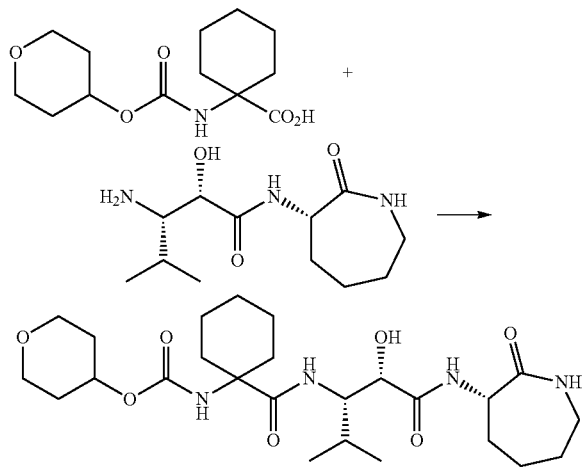

Using (2S,3S)-3-amino-N-[(3S)-hexahydro-2-oxo-1H-azepin-3-yl]-2-hydroxy-4-methylpentanamide (40.8 g, 159 mmol), the same procedure as in Production Example 3 was performed to produce 75.6 g (93%) of the title compound.

$^1$H-NMR (CDCl$_3$, δ):
0.90 (3H, d, J=7 Hz), 1.00 (3H, d, J=7 Hz), 1.24-2.07 (21H, m), 3.20-3.31 (2H, m), 3.45-3.54 (2H, m), 3.86-4.00 (3H, m), 4.23 (1H, dd, J=9 Hz, 3 Hz), 4.49 (1H, dd, J=10 Hz, 6 Hz), 4.68 (1H, d, J=9 Hz), 4.75-4.84 (1H, m), 5.10 (1H, s), 6.10 (1H, t, J=6 Hz), 7.20 (1H, d, J=8 Hz), 7.68 (1H, d, J=6 Hz)

Example 1

Production of [1-[[[(1S)-3-[[(3S)-hexahydro-2-oxo-1H-azepin-3-yl]amino]-1-(1-methylethyl)-2,3-dioxopropyl]amino]carbonyl]cyclohexyl]carbamic acid tetrahydro-2H-pyran-4-yl ester (compound 1)

[Chemical Formula 14]

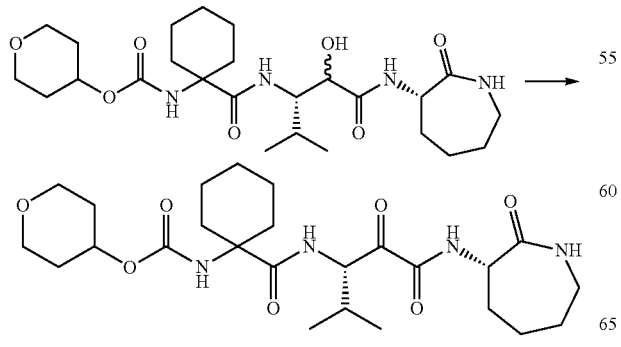

Under ice cooling, sulfur trioxide-pyridine (43.8 g, 275 mmol) was gradually added to a solution of [1-[[[(1S,2RS)-3-[[(3S)-hexahydro-2-oxo-1H-azepin-3-yl]amino]-2-hydroxy-1-(1-methylethyl)-3-oxopropyl]amino]carbonyl]cyclohexyl]carbamic acid tetrahydro-2H-pyran-4-yl ester (23.4 g, 45.9 mmol) and N,N-diisopropylethylamine (35.5 g, 275 mmol) in 150 ml of dry dimethyl sulfoxide and 50 ml of dry dichloromethane. The mixture was stirred at the same temperature for 1 hour. The reaction mixture was poured into ice-water and then extracted with dichloromethane. The organic layer was washed with a 20% citric acid aqueous solution, a saturated sodium hydrogen carbonate aqueous solution, and brine. After the organic layer wad dried over anhydrous sodium sulfate, the solvent was removed by distillation in vacuo. Ethyl acetate was added to the residue and stirred overnight. The precipitated crystals were separated by filtration to give 20.6 g (88%) of the title compound.

$^1$H-NMR (CDCl$_3$, δ):
0.81 (3H, d, J=7 Hz), 1.01 (3H, d, J=7 Hz), 1.25-2.14 (20H, m), 2.30-2.42 (1H, m), 3.22-3.34 (2H, m), 3.52 (2H, td, J=9 Hz, 3 Hz), 3.85-3.98 (2H, m), 4.45 (1H, ddd, J=11 Hz, 6 Hz, 2 Hz), 4.79-4.88 (1H, m), 4.93 (1H, s), 5.33 (1H, dd, J=8 Hz, 5 Hz), 6.31 (1H, t, J=6 Hz), 7.27 (1H, d, J=8 Hz), 8.18 (1H, d, J=6 Hz)

To determine the Rf value, thin layer chromatography (TLC) analysis was performed under the conditions below. The Rf value shown in the example below was also obtained under the same conditions.

TLC: HPTLC plates RP-18F254s manufactured by Merck KGaA
Developing solvent: acetonitrile:water=7:3
Rf value: 0.58

Production Example 5

Production of 1-[[[[1-(methoxycarbonyl)-4-piperidinyl]oxy]carbonyl]amino]cyclohexanecarboxylic acid

[Chemical Formula 15]

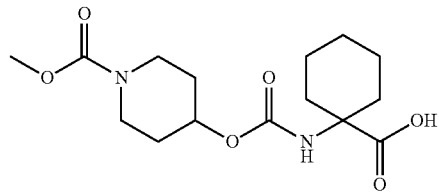

(1) Production of 1-[[[[1-[(1,1-dimethylethoxy)carbonyl]-4-piperidinyl]oxy]carbonyl]amino]cyclohexanecarboxylic acid benzyl ester

[Chemical Formula 16]

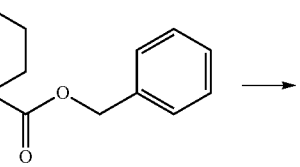

-continued

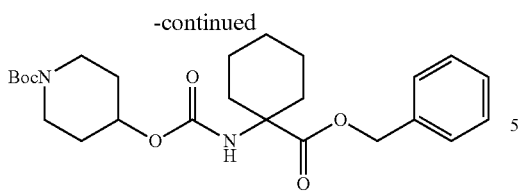

Benzyl 1-aminocyclohexanecarboxylate (9.27 g, 40 mmol) was added to a dichloromethane solution of di-tert-butyl dicarbonate (8.7 g, 40 mmol) and 4-dimethylaminopyridine (488 mg, 4 mmol) and stirred at room temperature for 30 minutes. The reaction mixture was concentrated in vacuo. To the residue were added 1-tert-butoxycarbonyl-4-hydroxypiperidine (16 g, 80 mmol) and N,N-diisopropylethylamine (10.3 g, 80 mmol) and stirred at 100° C. overnight. The reaction mixture was returned to room temperature and then diluted with ethyl acetate. The dilution was washed with a 10% potassium hydrogen sulfate aqueous solution, a saturated sodium hydrogen carbonate aqueous solution, and brine. After the organic layer was dried over anhydrous sodium sulfate, the solvent was removed by distillation in vacuo. The residue was purified by silica gel column chromatography to give 16 g (87%) of the title compound.

$^1$H-NMR (CDCl$_3$, δ):
1.21-2.10 (14H, m), 1.46 (9H, s), 3.05-3.23 (2H, m), 3.65 (2H, br-s), 4.67-4.80 (1H, m), 4.86 (1H, br-s), 5.13 (2H, s), 7.23-7.40 (5H, m)

(2) Production of 1-[[(4-piperidinyloxy)carbonyl]amino]cyclohexanecarboxylic acid benzyl ester hydrochloride

[Chemical Formula 17]

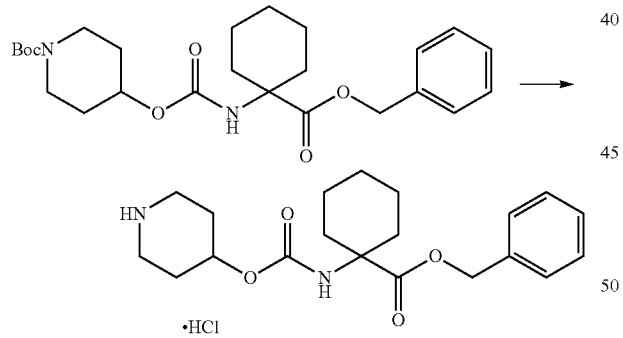

Four M hydrochloric acid/dioxane was added to 1-[[[1-[(1,1-dimethylethoxy)carbonyl]-4-piperidinyl]oxy]carbonyl]amino]cyclohexanecarboxylic acid benzyl ester (16 g, 34.7 mmol) and allowed to stand at room temperature for 2 hours. The reaction mixture was concentrated in vacuo. Ethyl acetate was added to the resulting residue. The resulting suspension was stirred for 2 hours. The resulting crystals were separated by filtration and dried in vacuo to give 12 g (87%) of the title compound.

$^1$H-NMR (DMSO-d$_6$, δ):
1.12-1.30 (1H, m), 1.45-1.59 (5H, m), 1.60-1.78 (4H, m), 1.83-2.02 (4H, m), 2.90-3.02 (2H, m), 3.05-3.20 (2H, m), 4.65-4.74 (1H, m), 5.05 (2H, s), 7.28-7.42 (5H, m), 7.59 (1H, s)

(3) Production of 1-[[[[1-(methoxycarbonyl)-4-piperidinyl]oxy]carbonyl]amino]cyclohexanecarboxylic acid benzyl ester

[Chemical Formula 18]

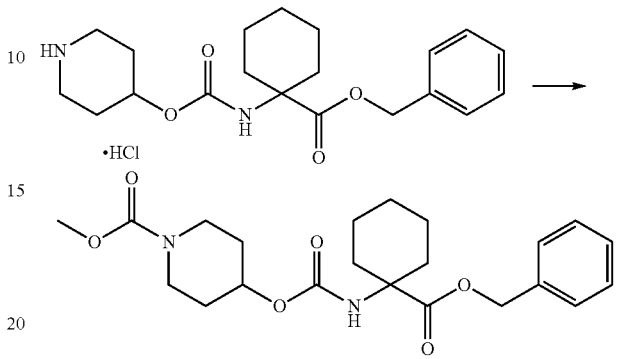

Under ice cooling, methyl chloroformate (378 mg, 4.0 mmol) was added to a methylene chloride solution of 1-[[(4-piperidinyloxy)carbonyl]amino]cyclohexanecarboxylic acid benzyl ester hydrochloride (1.59 g, 4.0 mmol) and triethylamine (2 g, 20 mmol). The mixture was stirred at room temperature overnight. Water was added to the reaction mixture, and the mixture was extracted with ethyl acetate. The organic layer was separated and then washed with a 10% potassium hydrogen sulfate aqueous solution, a saturated sodium hydrogen carbonate aqueous solution, and brine. After the organic layer was dried over anhydrous sodium sulfate, the solvent was removed by distillation in vacuo. Diisopropyl ether was added to the resulting residue, and the resulting suspension was stirred overnight. The resulting crystals were separated by filtration and dried in vacuo to give 1.67 g (quantitative) of the title compound.

$^1$H-NMR (CDCl$_3$, δ):
1.21-2.11 (14H, m), 3.08-3.31 (2H, m), 3.51-3.79 (2H, m), 3.69 (3H, s), 4.65-4.82 (1H, m), 4.87 (1H, br-s), 5.31 (2H, s), 7.12-7.39 (5H, m)

(4) Production of 1-[[[[1-(methoxycarbonyl)-4-piperidinyl]oxy]carbonyl]amino]cyclohexanecarboxylic acid

[Chemical Formula 19]

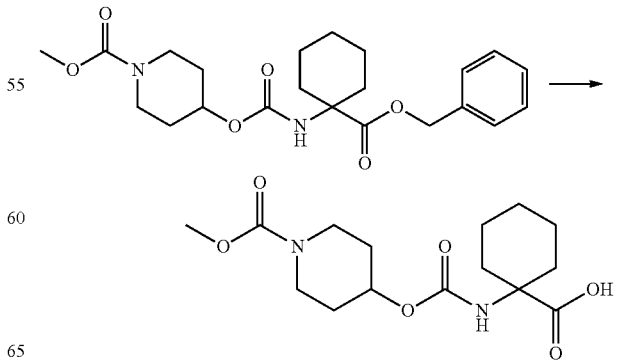

To an ethyl acetate solution of 1-[[[[1-(methoxycarbonyl)-4-piperidinyl]oxy]carbonyl]amino]cyclohexanecarboxylic acid benzyl ester (1.68 g, 4 mmol) was added 10% palladium-carbon (168 mg) and stirred at room temperature under a hydrogen gas atmosphere overnight. The insoluble matter was removed by filtration, and the filtrate was concentrated in vacuo. Diisopropyl ether was added to the residue, and the resulting suspension was stirred overnight. The resulting crystals were separated by filtration and dried in vacuo to give 1.01 g (75%) of the title compound.

¹H-NMR (CDCl₃, δ):

1.21-2.18 (14H, m), 3.26 (2H, br-s), 3.48 (1H, br-s), 3.69 (3H, s), 3.61-3.89 (2H, m), 4.83 (1H, br-s), 4.94 (1H, br-s)

Production Example 6

Production of [1-[[[(1S,2S)-3-[[(3S)-hexahydro-2-oxo-1H-azepin-3-yl]amino]-2-hydroxy-1-(1-methylethyl)-3-oxopropyl]amino]carbonyl]cyclohexyl]carbamic acid 1-(methoxycarbonyl)-4-piperidinyl ester

[Chemical Formula 20]

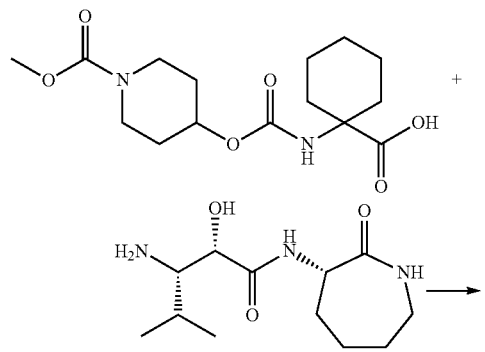

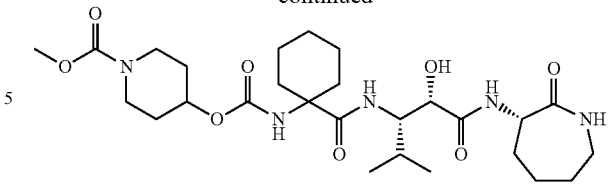

Under ice cooling, 1-ethyl-3-(3-dimethylaminopropyl)carbodiimide hydrochloride (316 mg, 1.65 mmol) was added to a methylene chloride solution of 1-[[[[1-(methoxycarbonyl)-4-piperidinyl]oxy]carbonyl]amino]cyclohexanecarboxylic acid (493 mg, 1.5 mmol), (2S,3S)-3-amino-N-[(3S)-hexahydro-2-oxo-1H-azepin-3-yl]-2-hydroxy-4-methylpentanamide (386 mg, 1.5 mmol), and 1-hydroxybenzotriazole (241 mg, 1.57 mmol). The liquid mixture was returned to room temperature and stirred overnight. The reaction mixture was diluted with methylene chloride. The dilution was washed with a 10% potassium hydrogen sulfate aqueous solution, a saturated sodium hydrogen carbonate aqueous solution, and brine. After the organic layer was dried over anhydrous sodium sulfate, the solvent was removed by distillation in vacuo. Diisopropyl ether was added to the resulting residue, and the resulting suspension was stirred overnight. The resulting crystals were separated by filtration and dried in vacuo to give 795 mg (93%) of the title compound.

¹H-NMR (CDCl₃, δ):

0.90 (3H, d, J=7 Hz), 1.00 (3H, d, J=7 Hz), 1.18-2.17 (21H, m), 3.18-3.38 (4H, m), 3.68 (3H, s), 3.59-3.85 (1H, m), 3.92-4.05 (1H, m), 4.18-4.28 (1H, m), 4.41-4.52 (1H, m), 4.60-4.73 (1H, m), 4.73-4.85 (1H, m), 5.14 (1H, s), 6.20-6.31 (1H, m), 7.20 (1H, br-s), 7.68 (1H, br-s)

Example 2

Production of [1-[[[(1S)-3-[[(3S)-hexahydro-2-oxo-1H-azepin-3-yl]amino]-1-(1-methylethyl)-2,3-dioxopropyl]amino]carbonyl]cyclohexyl]carbamic acid 1-(methoxycarbonyl)-4-piperidinyl ester (compound 2)

[Chemical Formula 21]

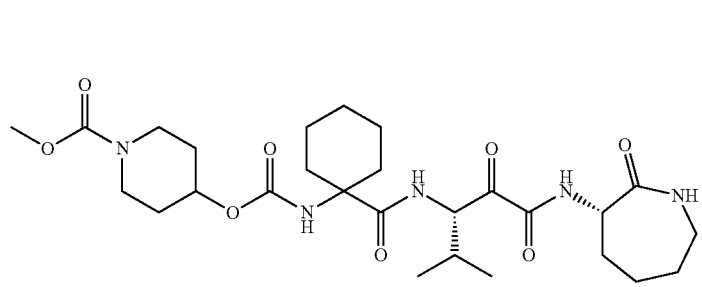

To a dimethyl sulfoxide solution of [1-[[[(1S,2S)-3-[[(3S)-hexahydro-2-oxo-1H-azepin-3-yl]amino]-2-hydroxy-1-(1-methylethyl)-3-oxopropyl]amino]carbonyl]cyclohexyl]carbamic acid 1-(methoxycarbonyl)-4-piperidinyl ester (795 mg, 1.4 mmol) was added 2-iodoxybenzoic acid (1.96 g, 7.0 mmol). After the mixture was stirred at room temperature for 2 hours, ethyl acetate and water were added to the reaction mixture. Sodium thiosulfate was then added to the mixture until a clear solution was obtained. After the organic and aqueous layers were allowed to separate, the organic layer was washed sequentially with a saturated sodium hydrogen carbonate aqueous solution and brine. After the resulting organic layer was dried over sodium sulfate, the solvent was removed by distillation in vacuo. The resulting residue was purified by silica gel column chromatography to give 516 mg (65%) of the title compound.

$^1$H-NMR (CDCl$_3$, δ):
0.79 (3H, d, J=7 Hz), 1.01 (3H, d, J=7 Hz), 1.20-2.21 (20H, m), 2.30-2.41 (1H, m), 3.18-3.38 (4H, m), 3.67 (3H, s), 3.62-3.93 (1H, m), 4.53 (1H, dd, J=10 Hz, 6 Hz), 4.78-4.90 (1H, m), 4.89 (1H, s), 5.23-5.40 (1H, m), 6.02-6.18 (2H, m), 7.18-7.29 (1H, m), 8.17 (1H, d, J=6 Hz) Rf value: 0.68

TEST EXAMPLES

As described below, cathepsin K inhibitory activity and bone resorption inhibitory activity were measured according to the method shown in JP 2000-204071 A. Comparative compounds 1 to 15 shown below are the top 15 compounds showing good results among the cyclic amide derivative compounds that are disclosed as having high bone resorption inhibitory activity in low-calcium diet mice in JP 2000-204071 A (Patent Literature 1).

Comparative compound 1: the compound of Example 120 in Patent Literature 1
Comparative compound 2: the compound of Example 5 in Patent Literature 1
Comparative compound 3: the compound of Example 140 in Patent Literature 1
Comparative compound 4: the compound of Example 121 in Patent Literature 1
Comparative compound 5: the compound of Example 82 in Patent Literature 1
Comparative compound 6: the compound of Example 97 in Patent Literature 1
Comparative compound 7: the compound of Example 92 in Patent Literature 1
Comparative compound 8: the compound of Example 33 in Patent Literature 1
Comparative compound 9: the compound of Example 131 in Patent Literature 1
Comparative compound 10: the compound of Example 64 in Patent Literature 1
Comparative compound 11: the compound of Example 34 in Patent Literature 1
Comparative compound 12: the compound of Example 81 in Patent Literature 1
Comparative compound 13: the compound of Example 6 in Patent Literature 1
Comparative compound 14: the compound of Example 135 in Patent Literature 1
Comparative compound 15: the compound of Example 27 in Patent Literature 1

As to cathepsin K inhibitory activity, comparative compounds 1 to 15 and compounds according to the present invention (compounds 1 and 2 shown below are the compounds obtained in Examples 1 and 2, respectively) were measured for IC$_{50}$ value (50% inhibitory concentration). As to bone resorption inhibitory activity, only the compounds of the present invention were subjected to the measurement, while the data shown in JP 2000-204071 were used with respect to comparative compounds 1 to 15.

As to CYP3A4 inhibitory activity, comparative compounds 1 to 15 and the compounds of the present invention were each measured for DI (direct inhibition) and MBI (mechanism based inhibition), and the IC$_{50}$ value for DI and MBI was each calculated.

On the basis of these data, calculations were made to determine the ratio (CYP/CatK) between the IC$_{50}$ values for CYP3A4 inhibitory activity (MBI) and the IC$_{50}$ values for cathepsin K inhibitory activity with respect to the comparative compounds and the compounds of the present invention, and the selectivity for the target enzyme cathepsin K was evaluated.

Test Example 1

Measurement of Cathepsin K Inhibitory Activity

Cathepsin K was prepared as follows. The proenzyme of cathepsin K was produced in cell culture media using a baculovirus expression system in Sf21 insect cells and then incubated at 40° C. for 1 hour to form the active enzyme (Tezuka et al., J. Biol. Chem., 269, 1106-1109 (1994)). The activity of cathepsin K was measured from the decomposition of the fluorescent substrate Z-Gly-Pro-Arg-MCA (3208-v from PEPTIDE INSTITUTE, INC.) according to the method of Aibe et al. (Aibe et al., Biol. Pharm. Bull., 19, 1026-1031 (1996)). Specifically, the decomposition of 20 μM Z-Gly-Pro-Arg-MCA by cathepsin K was measured in 100 mM potassium sodium phosphate, 1 mM EDTA, 8 mM Cysteine, pH 6.0. The reaction was performed at 37° C. for 30 minutes and then quenched by the addition of $2\times10^{-5}$ M of calpeptin. After the reaction was quenched, the intensity of fluorescence was measured at an excitation wavelength of 355 nm and a measurement wavelength of 460 nm.

As to the measurement results, Tables 3 and 4 show the IC$_{50}$ values (nmol/L) of the comparative compounds and the compounds of the present invention, respectively, together with the results of other test examples.

Test Example 2

Measurement of Bone Resorption Inhibitory Activity

The measurement was performed by the same method as described in JP 2000-204071 A (Patent Literature 1). Specifically, male mice (23 to 25 g weight, 8 mice per group) were fed with low-calcium diet (0.1% calcium diet) for 7 days. After overnight fasting, the compound of the present invention was orally administered to the mice at 100 mg/kg weight, and 4 hours after the administration, the calcium concentration of the serum was measured by the methyl xylenol blue method (Biochem Biophys Res Commun., 125, 441-447 (1984), FEBS Lett., 321(2-3), 247-250 (1993)). The rate (%) of decrease in serum calcium was determined by comparison with the control group.

Tables 3 and 4 show the results of the measurement of the comparative compounds and the compounds of the present invention, respectively, together with the results of other tests. It should be noted that the data of the rate (%) of decrease in serum calcium as to comparative compounds 1 to 15 are the values shown in JP 2000-204071 A (Patent Literature 1).

Test Example 3

Measurement of CYP3A4 Inhibitory Activity

The measurement of CYP3A4 inhibitory activity was performed with reference to the method of Newton et al. (Drug Metab. Dispos. 23, 154-158 (1995)) and the method described in JP 2007-236327 A.

A reaction mixture was prepared by mixing the compound of the present invention with midazolam as a typical substrate for CYP3A4 (see Food and Drug Administration (FDA) Guidance for Industry Drug Interaction Studies—Study Design, Data Analysis, Implications for Dosing, and Labeling Recommendations. FDA web site [online], www.fda.gov/downloads/drugs/guidancecomplianceregulatoryinformation/guidances/ucm292362.pdf), coenzyme NADPH-generating system, human hepatic microsomes, and a phosphate buffer. The reaction mixture was incubated at 37° C. for 10 minutes. Table 1 below shows the solutions used in the preparation of the coenzyme NADPH-generating system solution.

TABLE 1

| Compound Name | Solvent | Prepared Concentration |
|---|---|---|
| β-Nicotinamide adenine dinucleotide phosphate (β-NADP+) | Phosphate Buffer (pH 7.4) | 13 mmol/L |
| glucose-6-phosphate (G-6-P) | Phosphate Buffer (pH 7.4) | 33 mmol/L |
| glucose-6-phosphate dehydrogenase (G-6-P DH(Y)) | Phosphate Buffer (pH 7.4) | 10 U/mL |
| MgCl$_2$ | Phosphate Buffer (pH 7.4) | 33 mmol/L |

The coenzyme NADPH-generating system solution was prepared by mixing the materials shown in Table 1: the 13 mmol/L β-NADP+ solution, the 33 mmol/L G-6-P solution, the solution of 10 U/mL G6PDH (Y) (manufactured by Oriental Yeast Co., Ltd.), and the 33 mmol/L MgCl$_2$ solution in a ratio of 1:1:0.4:1 (v:v:v:v). Table 2 below shows the composition of the reaction mixture used in the measurement of CYP3A4 inhibitory activity. The final concentrations of the compounds of the present invention and the comparative compounds were set at the levels considered to be necessary for the calculation of the IC$_{50}$ values based on the results of the measurement performed at an arbitrary concentration in advance.

TABLE 2

| Solution | Added Amount (μL) | Final Concentration |
|---|---|---|
| Inventive Compound or Comparative Compound | 5 | It was set at the level necessary for the calculation of the IC$_{50c}$ value. |
| Midazolam Solution | 10 | 1000 nmol/L |
| 0.1M Phosphate Buffer (pH 7.4) | 265 | — |

TABLE 2-continued

| Solution | Added Amount (μL) | Final Concentration |
|---|---|---|
| Coenzyme NADPH-Generating System Solution | 170 | β-NADP+ 1.3 mmol/L<br>G-6-P 3.3 mmol/L<br>G-6-P DH(Y) 0.4 U/mL<br>MgCl$_2$ 3.3 mmol/L |
| Diluted Microsomes | 50 | 0.1 mg protein/mL |

After the incubation, the reaction was quenched by the addition of an acetonitrile solution to the reaction mixture. The amount of 1'-hydroxymidazolam produced (the metabolite produced from midazolam by CYP3A4) was measured in the quenched sample with a high-performance liquid chromatography tandem mass spectrometer (LC-MS/MS). Each IC$_{50}$ value for DI (direct inhibition) was determined from the amount of the produced 1'-hydroxymidazolam and the final concentration of the compound of the present invention or the comparative compound in the reaction mixture.

MBI (mechanism based inhibition) was evaluated as follows. After the reaction mixture not containing midazolam (but containing the compound of the present invention or the comparative compound, the coenzyme NADPH-generating system, the human hepatic microsomes, and the phosphate buffer) was pre-incubated at 37° C. for 30 minutes, midazolam was added to the reaction mixture. The reaction mixture was then incubated at 37° C. for 10 minutes. Subsequently, the reaction was quenched by the addition of an acetonitrile solution to the reaction mixture. The amount of 1'-hydroxymidazolam produced was measured in the quenched sample with an LC-MS/MS. As in the case of DI, each IC$_{50}$ value for MBI was determined from the amount of the produced 1'-hydroxymidazolam and the final concentration of the compound of the present invention or the comparative compound in the reaction mixture.

Tables 3 and 4 show the results of the measurement of the comparative compounds and the compounds of the present invention, respectively, together with the results of other tests.

TABLE 3

| Comparative Compound | Rate of Decrease in Serum Ca (%) | CatK Inhibitory IC$_{50}$ (nmol/L) | CYP3A4 Inhibitory IC$_{50}$ (μmol/L) | | CYP/CatK |
|---|---|---|---|---|---|
| | | | DI | MBI | |
| 1 | 5.39 | 16 | 11.7 | 3.36 | 207 |
| 2 | 4.71 | 13 | 9.31 | 1.53 | 122 |
| 3 | 4.50 | 3.4 | 0.180 | 0.0373 | 11 |
| 4 | 4.48 | 7.4 | 12.6 | 2.16 | 291 |
| 5 | 4.38 | 26 | 14.0 | 4.59 | 179 |
| 6 | 4.33 | 20 | 8.28 | 2.07 | 103 |
| 7 | 4.08 | 23 | 23.7 | 4.41 | 193 |
| 8 | 4.07 | 7.8 | 15.5 | 2.57 | 328 |
| 9 | 3.97 | 39 | 0.723 | 0.0924 | 2 |
| 10 | 3.60 | 16 | 15.5 | 3.85 | 246 |
| 11 | 3.50 | 5.4 | 10.8 | 2.07 | 384 |
| 12 | 3.50 | 3.6 | 5.23 | 0.985 | 274 |
| 13 | 3.46 | 6 | 2.78 | 2.23 | 370 |
| 14 | 3.37 | 4.8 | 0.994 | 0.152 | 31 |
| 15 | 3.26 | 12 | 16.0 | 4.97 | 401 |

TABLE 4

| Inventive Compound | Rate of Decrease in Serum Ca (%) | CatK Inhibitory IC$_{50}$ (nmol/L) | CYP3A4 Inhibitory C$_{50}$ (μmol/L) DI | MBI | CYP/CatK |
|---|---|---|---|---|---|
| Compound 1 | 6.2 | 0.56 | >100 | 80.0 | 141739 |
| Compound 2 | 5.6 | 0.52 | 55.6 | 23.0 | 44231 |

These results show that all the comparative compounds have an IC$_{50}$ value (MBI) of less than 10 μM for CYP3A4 inhibition whereas the compounds of the present invention have an IC$_{50}$ value of more than 20 μM for CYP3A4 inhibition.

Therefore, according to the above-mentioned classification of the intensity of CYP3A4 inhibition, all the comparative compounds are determined to have at least a medium level of CYP3A4 inhibitory activity, whereas the compounds of the present invention are determined to have a low level of CYP3A4 inhibitory activity.

The enzyme selectivity (CYP/CatK) of the compounds of the present invention is calculated to be a value of more than 40,000 whereas that of the comparative compounds is calculated to be a value of less than about 400.

The invention claimed is:

1. A method for treating osteoporosis in a subject comprising administering to the subject a pharmaceutical composition comprising a compound of formula (I):

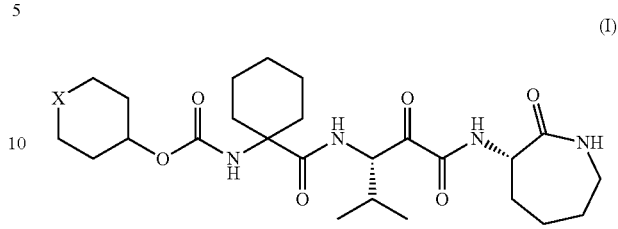

(I)

wherein X is —O— or —N(R$^1$)—, wherein R$^1$ is a (C1 to C10 alkoxy)carbonyl group,
and a pharmaceutically acceptable carrier, thereby treating osteoporosis in the subject.

2. The method of claim 1, wherein in formula (I), X is —O—.

3. The method of claim 1, wherein in formula (I), X is —N(R$^1$)—, wherein R$^1$ is a (C1 to C10 alkoxy)carbonyl group.

4. The method of claim 3, wherein R$^1$ is a methoxycarbonyl group.

* * * * *